(12) United States Patent
Søe et al.

(10) Patent No.: US 8,956,670 B2
(45) Date of Patent: *Feb. 17, 2015

(54) METHOD FOR THE CONTROL OF THE FORMATION OF ACRYLAMIDE IN A FOODSTUFF

(75) Inventors: Jørn Borch Søe, Tilst (DK); Lars Wexøe Petersen, Muskego, WI (US); Charlotte Horsmans Poulsen, Brabrand (DK); Thomas Rand, Copenhagen S (DK); Dana L. Boll, Olathe, KS (US)

(73) Assignee: Dupont Nutrition Bioscience APS, Copenhagen (DK)

( * ) Notice: Subject to any disclaimer, the term of this patent is extended or adjusted under 35 U.S.C. 154(b) by 0 days.

This patent is subject to a terminal disclaimer.

(21) Appl. No.: 13/433,470

(22) Filed: Mar. 29, 2012

(65) Prior Publication Data

US 2012/0244252 A1    Sep. 27, 2012

Related U.S. Application Data

(63) Continuation of application No. 11/048,230, filed on Feb. 1, 2005, now Pat. No. 8,163,317, which is a continuation-in-part of application No. 10/001,136, filed on Nov. 15, 2001, now Pat. No. 6,872,412, which is a continuation-in-part of application No. PCT/IB03/05278, filed on Oct. 24, 2003.

(60) Provisional application No. 60/438,852, filed on Jan. 9, 2003, provisional application No. 60/256,902, filed on Dec. 19, 2000.

(30) Foreign Application Priority Data

Nov. 17, 2000   (GB) .................................. 0028119.6
Oct. 30, 2002   (GB) .................................. 0225236.9

(51) Int. Cl.

| A23L 1/015 | (2006.01) |
|---|---|
| A23L 1/105 | (2006.01) |
| A23L 1/325 | (2006.01) |
| A23L 1/31 | (2006.01) |
| A23L 1/216 | (2006.01) |
| A23L 1/16 | (2006.01) |
| A21D 8/04 | (2006.01) |
| A23L 1/317 | (2006.01) |
| A23C 19/06 | (2006.01) |
| A23C 19/09 | (2006.01) |
| A23L 1/217 | (2006.01) |
| A23L 1/27 | (2006.01) |

(52) U.S. Cl.
CPC ......... *C12Y 101/03004* (2013.01); *A21D 8/042* (2013.01); *A23C 19/061* (2013.01); *A23C 19/063* (2013.01); *A23C 19/0912* (2013.01); *A23L 1/0153* (2013.01); *A23L 1/217* (2013.01); *A23L 1/27* (2013.01); *C12Y 101/03005* (2013.01); *C12Y 101/03009* (2013.01); *C12Y 111/01006* (2013.01); *A23V 2002/00* (2013.01)
USPC ........ 426/7; 426/28; 426/52; 426/56; 426/59; 426/531

(58) Field of Classification Search
CPC ........... A23V 2002/00; A23V 2200/48; A23L 1/0153; A23L 1/217; C12Y 101/03005; A21D 8/042
USPC .............................. 426/7, 28, 52, 56, 59, 531
See application file for complete search history.

(56) References Cited

U.S. PATENT DOCUMENTS

| 4,959,212 | A | 9/1990 | Stancesco et al. |
|---|---|---|---|
| 5,010,007 | A | 4/1991 | Prieels |
| 5,626,893 | A | 5/1997 | Reddy |
| 6,358,543 | B1 | 3/2002 | Soe et al. |
| 6,872,412 | B2 | 3/2005 | Soe et al. |
| 2002/0004085 | A1 | 1/2002 | Xu |
| 2002/0114864 | A1 | 8/2002 | Soe et al. |

FOREIGN PATENT DOCUMENTS

| EP | 0492716 | 12/1991 |
|---|---|---|
| EP | 1020523 | 7/2000 |
| GB | 740379 | 11/1955 |
| GB | 967574 | 8/1964 |
| JP | 48016612 | 5/1973 |
| JP | 09-009862 | 1/1997 |
| SU | 926004 | 5/1982 |
| WO | WO 89/11227 | 11/1989 |
| WO | WO 90/04336 | 5/1990 |
| WO | WO 96/39851 | 12/1996 |

(Continued)

OTHER PUBLICATIONS

Jiang, Z. et al. 1989. Reduction of nonenzymatic browning in potato chips and French fries with glucose oxidase. J. Food. Proc. Perserv. 13: 175-186.*
Acrylamide from Maiilard reaction products. Nature. 2002. 419: 449-450.*
Hansen, O. C. et al. 1997. Hexose oxidase from the Red Alga *Chondrus crispus*. J. Biol. Chem. 272: 11581-11587.*
Nature, 419: 449-450 (2002).*
Biekman E.S.A, Toepassing Van Enzymen Bij De Verwerking Van Aardappelen Tot Consumptierprodukten, Voedingsmiddelen Technologie, Noordervliet B.V. Zeist, NL, 1989, 22(20):51-53. English abstract enclosed.
Cook M.W. et al., Safety evaluation of a hexose oxidase expressed in *Hansenula polymorpha*, Food and Chemical Toxology, 2003, 41(4):523.
Whitaker J.R. et al., Handbook of food enzymology, Marcel Dekker Inc., New York, 2002, p. 429.

(Continued)

*Primary Examiner* — Hamid R Badr
(74) *Attorney, Agent, or Firm* — Vedder Price P.C.; Thomas J. Kowalski

(57) ABSTRACT

There is provided a process for the prevention and/or reduction of acrylamide formation and/or acrylamide precursor formation in a foodstuff containing (i) a protein, a peptide or an amino acid and (ii) a reducing sugar, the process comprising contacting the foodstuff with an enzyme capable of oxidizing a reducing group of the sugar.

7 Claims, 13 Drawing Sheets

(56) References Cited

FOREIGN PATENT DOCUMENTS

| WO | WO 96/40935 | 12/1996 |
|---|---|---|
| WO | WO 99/31990 | 7/1999 |

OTHER PUBLICATIONS

Mottram, et al. Acrylamide is formed in the Maillard reaction, Nature, 2002, 419:448.
Experimental data entitled "Effect of Different Hexose Oxidase and Other Oxido Reductases in Dough," Jun. 24, 2002.
Experimental data entitled Effect on Dough of HOX and GOX on maltose in Dough, Aug. 4, 2003.
Experimental data Investigation of Glucose Oxidase from *Cladosporium* Oxyporum (no date provided).
Jiang, Z. et al., Reduction of nonenzymatic browning in potato chips and French fries with glucose oxidase, J. Food Process. Preserv., 13(3): 175-86, 1989.
H.-D. Belitz & W. Grosch, Food Chemistry, Published 1987, Springer-Verlag, pp. 119-120.
Shipe, W.F., Enzymatic Modification of Milk Flavor; American Chemical Society, 1976(47), pp. 57-65.
Stadler, et al., Acrylamide From Maillard Reaction Products, Nature Publishing Group (2002), pp. 449.
Sols, A. et. al. (1957). On the substrate specificity of glucose oxidase. Biochim. Biophys. Acta, vol. 24, p. 206-207.
Printout from the American Chemical Society website entitled "Chemistry Comes Alive!", Journal of Chemical Education 2001, vol. 5 Glucose Oxidase http://jchemed.chem.wisc.edu/JCESoft/CCA/CCA5/MAIN/2BIOCHEM2/GLUOXID/GLUOXID3/MOVIE.HTM.
Schoevaart, R., et.al.(2002). Galactose dialdehyde as potential protein cross-linker: proof of principle, Carbohydrate Research, vol. 337, p. 899-904.
Fox, P.F. (1997). Chemistry of the Maillard Reaction: Reaction mechanisms and pathways. Advanced Dairy Chemistry, vol. 3, p. 167-168.
D.J. Dawson, Fermentation Studies on Thermoduric Starters used in High-Temperature Cheddar Cheese Manufacture, Australian Journal of Dairy Technology, Jul.-Sep. 1958, pp. 139-143.
M.A. Thomas, "Browning Reaction in Cheddar Cheese", Australian Journal of Dairy Technology, Dec. 1969, pp. 185-189.
M.E. Bley et al., "Factors Affecting Nonenzymatic Browning of Process Cheese", J. Dairy Science, 1985, vol. 68, pp. 555-561.
Mark E. Johnson et al., "Nonenzymatic Browning of Mozzarella Cheese", J. Dairy Science, 1985, vol. 68, pp. 3143-3147.
Edgar Spreer, "Compositions and characteristics of Milk", Milk and Dairy Product Technology, Marcel Dekker, Inc., 1998, pp. 22-23.
Don Scott, "Glucose Conversion in Preparation of Albumen Solids by Glucose-OxidaseCatalase System", Agricultural and Food Chemistry, Aug. 19, 1953, vol. 1, No. 11, pp. 727-730.
L.A. Underkofler, "Glucose Oxidase: Production, Properties, Present and Potential Applications", Soc. Chem. Ind., London, 1961, pp. 72-86.
Kelley, et al., Lignin, Pectin and Chitin, "Biomass", Methods in Enzymology, 1988, vol. 161, pp. 306-316.
Knull, et al., "Two dimensional paper chromatography for the detection of oxidation of maltose by glucose oxidase", J. Chromatog., 1971, vol. 55, pp. 425-428.
N. Low et al., "Reduction of Glucose Content in Potatoes with Glucose Oxidase", Journal of Food Science, 1989, vol. 54, No. 1, pp. 118-121.
Charlotte Poulsen et al., "Purification and Characterization of a Hexose Oxidase with Excellent Strengthening Effects in Bread", Cereal Chem., 1998, vol. 75, No. 1, pp. 51-57.
A.G. Rand Jr., "Direct Enzymatic Conversion of Lactose to Acid: Glucose Oxidase and Hexose Oxidase", Animal Science and Food & Resource Chemistry Departments, University of Rhode Island, 1972, vol. 37, pp. 698-701.
WPI Accession No. 1973-30288U.
Garcia. et al., Analysis and Modeling of the Ferulic Acid Oxidation . . . , J. Agric. Food Chem (2004) vol. 52. p. 3946-3953.
F. Giffhorn, Fungal Pyranose Oxidases: Occurance, Properties . . . , Appl. Microbiol. Biotechnol. (2000) vol. 54, p. 727-740.
John H. Pazur. et al., Comparison of the Action of Glucoamylase . . . , Carbohydrate Research (1977) vol. 58, p. 193-202.
L.A. Underkofler, Properties and Applications of the Fungal . . . , 1958 reprinted from Proceedings of the Int'l Symposium on Enzyme Chemistry, Tokyo and Koyoto 1957, p. 486-490.
Arjan van Wijk, et al., Enzymatically Oxidized Lactose and Derivatives . . . , Carbohydrate Research (2006) vol. 341. p. 2921-2926.
Gerald Reed (ed.), Enzymes in Food Processing, Academic Press (1975) p. 222-229.
Edwin C. Webb, Enzyme Nomenclature 1992, Academic Press, Inc., p. 56.
K. Kulp, Enzymes As Dough Improvers, Advances in Baking Technology, Ed. B.S. Kamel, et a!., Blackie Academic &Professional (1993) Chapter 7, p. 152 and 173.
Matzdorf, B. et al. 1994. Browning of mozzarella cheese during high temperature pizza baking. J. Dariy Science. 77:2850-2853.
Hansen, O. C. et al. 1997. Hexose oxidase from the red alga *Chondrus crispus*. J. Biological Chem. 272(17):11581-11587.
Appeal No. TI310/10-3309 European Patent No. 1341422 in the name of Danisco Aug. 27, 2010.
Opposition to EP No. 1341422 Jan. 8, 2010.

\* cited by examiner

METHOD FOR THE CONTROL OF THE FORMATION OF ACRYLAMIDE IN A FOODSTUFF

CROSS-REFERENCE TO RELATED APPLICATIONS

This application is a continuation of U.S. application Ser. No. 11/048,230 filed Feb. 1, 2005 now U.S. Pat. No. 8,163,317, which claims priority from U.S. application Ser. No. 10/001,136 filed Nov. 15, 2001, which claims priority from U.S. Provisional Application 60/256,902 filed Dec. 19, 2000 and United Kingdom Application 0028119.6 filed Nov. 17, 2000. U.S. application Ser. No. 11/048,230 filed Feb. 1, 2005 is also a continuation-in-part of International Patent Application No. PCT/IB2003/005278 filed Oct. 24, 2003 and published as WO 2004/039174 on May 13, 2004, which claims priority from United Kingdom Application 0225236.9 filed Oct. 30, 2002 and U.S. Provisional Application No. 60/438,852 filed Jan. 9, 2003. All of the above-mentioned applications, as well as all documents cited herein and documents referenced or cited in documents cited herein, are hereby incorporated herein in their entirety by reference.

FIELD OF THE INVENTION

The present invention relates to the control of the formation of acrylamide in a foodstuff.

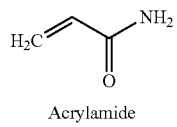

Acrylamide

BACKGROUND OF THE INVENTION

Acrylamide and polyacrylamide are used in industry for the production of plastics. It has been supposed that the main exposure for acrylamide in the general population has been through drinking water and tobacco smoking Exposure via drinking water is small and the EU has determined maximum levels of 0.1 microgram per liter water.

Acrylamide is water soluble and is quickly absorbed in the digestive tract. Excretion via the urine is fast and half of acrylamide is cleared from the body in a few hours.

The toxicological effects of acrylamide are well known. It causes DNA damage and at high doses neurological and reproductive effects have been observed. Glycidamide, a metabolite of acrylamide, binds to DNA and can cause genetic damage. Prolonged exposure has induced tumours in rats, but cancer in man has not been convincingly shown. The International Agency for Research on Cancer (IARC) has classified acrylamide as a "probably carcinogenic to humans" (Group 2A).

Acrylamide has been shown to induce gene mutations in cultured animal cells and also in animals treated in vivo. Thus it is assumed that exposure also to very low doses of acrylamide increases the risk for mutation and cancer.

High doses of acrylamide have been applied in the toxicological studies, which is an accepted practice. 25-50 mg per kg body weight is the lowest dose that has been shown to increase the mutation frequency in mouse. Recent studies in the laboratory of the Swedish Food Administration have shown that chromosome aberrations are induced in mice at 10-20 times lower doses.

Among the acrylamide metabolites glycidamide is considered the most likely candidate for causing genetic damage. Glycidamide has been found in mice and rats, and also in humans exposed to acrylamide.

Neurological damage was observed when rats were given acrylamide in their drinking water. The lowest effective dose was 2 mg/kg body weight and day, and the highest no-effect dose was 0.5 mg/kg body weight and day. Also humans exposed to high doses of acrylamide have shown neurological damage, e.g. some workers occupied in the building of the tunnel at Hallandsåsen. It is difficult to assess the highest acrylamide dose in humans that does not cause neurological effects (NOEL). The level is probably several times higher than the average acrylamide intake from food.

Decreased fertility was observed in rats exposed to 5-10 mg acrylamide/kg body weight and day.

Epidemiological studies in man have not shown a correlation between exposure to acrylamide and increased cancer rate. These studies have been criticised because the number of studied persons was too low considering the expected effect.

Two long-term studies in rats have shown a substantial increase of tumours in different organs when the animals were exposed to acrylamide in drinking water. Similar studies have been made in mice. The lowest effective dose was 2 mg/kg body weight per day.

In the studies with rats the increase of tumours was most evident in specific organs, e.g. mammary gland, uterus, adrenal gland, scrotal mesothelium. In mice there was an increase of lung and skin tumours. These cancer studies have been used for the assessment of the risk of cancer in humans due to acrylamide exposure.

It should be noted that the genotoxic studies have indicated that there is no threshold value for the risk of cancer induced by acrylamide, i.e. there is no dose of acrylamide so low that it does not increase the risk of cancer. In making these assessments it is assumed that man and rat have the same sensitivity for cancer induction by acrylamide.

The results of the risk assessments are somewhat different since they are based on different mathematical models. By consumption of 1 microgram acrylamide/kg body weight per day the lifetime risk for cancer has been calculated to 4.5 per 1000 (U.S. EPA)
0.7 per 1000 (WHO)
10 per 1000 (Granath et al. 1999, Stockholm University)

Recent analyses have now indicated that the exposure to acrylamide is probably considerably higher (for non-smokers) from consumption of certain foods that have been heated. As reported in J Agric Food Chem. 2002 Aug. 14; 50(17): 4998-5006 a group at the University of Stockholm, headed by Prof. Margareta Tornqvist, has found that acrylamide is formed during heating of starch-rich foods to high temperatures.

The Swedish National Food Administration has developed a LC/MS/MS-method for the analysis of acrylamide in foods. Analysis has shown that acrylamide is present in a large number of foods, including many regarded as staple foods. The levels of acrylamide differ widely within each food group analysed.

Using information on the levels in different foods and Swedish food consumption data, it is suggested that a significant number of annual cancer cases can be attributed to acrylamide.

When foodstuffs were analysed at the Swedish National Food Administration (NFA) in Uppsala and at AnalyCen AB in Lidkoping it was found that some foodstuffs, which had been heated, could contain relatively high levels of the substance acrylamide. In total, more than 100 food samples have been analysed at the NFA. The food survey comprised bread, pasta, rice, fish, sausages, meat (beef and pork), biscuits, cookies, breakfast cereals and beer, etc as well as some ready-made dishes such as pizza and products based on potatoes, maize and flour.

The levels of acrylamide vary considerably between single foodstuffs within food groups, but potato crisps and French fries generally contained high levels compared to many other food groups. The average content in potato crisps is approximately 1000 microgram/kg and in French fries approximately 500 microgram/kg. Other food groups which may contain low as well as high levels of acrylamide are crisp bread, breakfast cereals, fried potato products, biscuits, cookies and snacks, e.g. popcorn.

Foodstuffs which are not fried, deep fried or oven-baked during production or preparation are not considered to contain any appreciable levels of acrylamide. No levels could be detected in any of the raw foodstuffs or foods cooked by boiling investigated so far (potato, rice, pasta, flour and bacon).

According to the NFA food survey "Riksmaten 1997-98", which is based on approximately 1200 individuals between the age of 17 to 70 who recorded their food consumption during one week, an average intake of acrylamide of approximately 25 microgram per day (maximum intake is approximately six times higher) is obtained, based on the food groups shown below. The remaining food groups are estimated to account for approximately 10-15 microgram of acrylamide; in total an average intake of 35-40 microgram. The percentage contribution based on an intake of 40 microgram acrylamide per day results in:

potato products: 36% (French fries 16%, fried potatoes 10%, crisps 10%)
bread: 16%
biscuits, cookies and wafers: 5%
breakfast cereals: 3%
remaining foodstuffs groups, basically not investigated yet: 40%

Young adults (17 to 34 years of age) have, according to "Riksmaten", a higher consumption of snacks (nuts, chips and popcorn) than other adults. For children under 17 years of age newer data are lacking In the food survey "Ungdom mot år 2000" (Samuelson et al 1996), which was carried out 1993-94 among 15-year olds in Uppsala and Trollhättan, the consumption of snacks was comparable to that of young adults in Riksmaten. Children have a lower average body weight than the 70 kg generally assumed when carrying out risk assessments. This implies that the food intake per kg body weight and the exposure to various substances could be even larger for those groups of individuals compared to adults. According to Riksmaten, 10 percent of the adult population consumes 90 percent of the snacks consumed in Sweden.

An alternative way of estimating the intake of acrylamide is by adduct measurement, that is to measure a reaction product of acrylamide with the protein of the blood, the haemoglobin (Tornqvist et al 1997). This reaction product seems to occur in all investigated humans at approximately the same levels and is furthermore a measurement of the continuously administered dose of acrylamide. The reason is unknown in this case, but workers who were exposed to acrylamide at the tunnel accident at Hallandsåsen in Sweden had higher levels of this reaction product in their blood.

In the general population, although not in smokers (who have a level of this adduct 2-3 times the background level), the background level has been estimated to account for a daily intake corresponding to approximately 100 microgram per day.

Other sources than foodstuffs (estimated average intake of 35-40 μg/day), e.g. cosmetics, drinking water, and a possible endogenous formation in the body of acrylamide, could, to a lower extent contribute to the background level. Estimated administered amount of acrylamide for the formation of the background level together with levels of acrylamide in foodstuffs are, however, presently extremely uncertain.

A Report from Swedish Scientific Expert Committee entitled "Acrylamide In Food-Mechanisms of formation and influencing factors during heating of foods" discloses possible mechanisms for the formation of acrylamide in food. Relevant extracts from this report are given below in Appendix 1.

According to Health Canada, model experiments carried out in the Food Directorate showed that when asparagine is heated with glucose, acrylamide is produced. In an open letter, Health Canada stated "The production of acrylamide in these studies was temperature dependent and gave comparable results to those found when potato slices were similarly heated. At this time, not much is known about other possible pathways of formation of acrylamide in foods."

Further discussion of reactions occurring during heating of food is given in Principles of Food Chemistry pages 100-109. This discussion is provided in Appendix 2.

The present invention alleviates the problems of the prior art.

Some aspects of the invention are defined in the appended claims.

BRIEF SUMMARY OF THE INVENTION

In one aspect the present invention provides a process for the prevention and/or reduction of acrylamide formation and/or acrylamide precursor formation in a foodstuff containing (i) a protein, a peptide or an amino acid and (ii) a reducing sugar, the process comprising contacting the foodstuff with an enzyme capable of oxidising a reducing group of the sugar.

In one aspect the present invention provides use of an enzyme for the prevention and/or reduction of acrylamide formation and/or acrylamide precursor formation in a foodstuff containing (i) a protein, a peptide or an amino acid and (ii) a reducing sugar, wherein the enzyme is capable of oxidising a reducing group of the sugar.

Acrylamide formation and/or acrylamide precursor formation in cooked foodstuffs, in particular starch foodstuffs and foodstuffs containing a protein/amino acid/peptide and reducing sugar is described in Appendices 1 and 2, for example by the Amadori reaction, and is known in the art. In such foodstuffs a sugar such as glucose, galactose and/or maltose may react with an amino acid such as asparagine, glutamic acid, lysine, or arginine. Any primary amine capable of nucleophilic attack on the carbonyl group of a reducing sugar may be involved This reaction may be an important step in the formation of acrylamide.

The present invention prevents and/or reduces the problematic condensation reactions between amino acids, in particular the amino group thereof, and reducing sugars which result in acrylamide or acrylamide precursor formation. These reactions may comprise the Amadori reaction, Heynes rearrangements, or reaction cascades resulting from the Maillard reaction. The present invention may prevent and/or reduce the reaction which directly results in acrylamide formation. It may also prevent and/or reduce reaction(s) which provide materials which further react to provide acrylamide, namely acrylamide precursors. Acrylamide precursors are often provided by degradation of carbohydrates. A typical acrylamide precursor is 2-propenal.

The problems of the formation of acrylamide and/or acrylamide precursor formation in foodstuffs containing a protein and a reducing sugar such as baked food products, in particular formation caused either completely or in part by the Amadori reaction, can be controlled by contacting the foodstuff with an enzyme capable of oxidising the reducing group of the sugar. This is a novel approach in which reducing sugar is oxidised to avoid acrylamide formation and/or acrylamide precursor formation by bringing the foodstuff into contact with an enzyme which is capable of performing the necessary oxidation and thereby eliminating the reducing sugar from the foodstuff by conversion.

In the present specification, by the term "prevention and/or reduction of acrylamide formation" it is meant that the amount of acrylamide produced is reduced and/or the period of time required for formation of a given amount of acrylamide is increased.

In some aspects preferably the process prevents and/or reduces Amadori reaction in a foodstuff.

Thus in one aspect the present invention provides a process for the prevention and/or reduction of Amadori reaction in a foodstuff containing (i) a protein, a peptide or an amino acid and (ii) a reducing sugar, the process comprising contacting the foodstuff with an enzyme capable of oxidising a reducing group of the sugar.

In one further aspect the present invention provides use of an enzyme for the prevention and/or reduction of Amadori reaction in a foodstuff containing (i) a protein, a peptide or an amino acid and (ii) a reducing sugar, wherein the enzyme is capable of oxidising a reducing group of the sugar.

In the present specification, by the term "prevention and/or reduction of Amadori reaction" it is meant that the extent of a Amadori reaction is reduced and/or the period of time required for completion of a Amadori reaction is increased.

In some aspects preferably the enzyme is capable of oxidising the reducing group of a monosaccharide and the reducing group of a disaccharide.

In some aspects preferably the enzyme is hexose oxidase (EC1.1.3.5) or glucose oxidase (EC 1.1.3.4). In a highly preferred aspect the enzyme is hexose oxidase. Preferably the HOX is obtained or prepared in accordance with WO 96/40935. Preferably the HOX is DairyHOX™ available from Danisco A/S, Denmark.

In some aspects preferably the enzyme may oxidise matlodextrins and/or celludextrins. In a preferred aspect the enzyme is a carbohydrate oxidase which may oxidise matlodextrins and/or celludextrins. Preferably the carbohydrate oxidase is obtained or prepared in accordance with WO 99/31990.

Hexose oxidase (HOX) is a carbohydrate oxidase originally obtained from the red alga *Chondrus crispus*. As discussed in WO 96/39851 HOX catalyses the reaction between oxygen and carbohydrates such as glucose, galactose, lactose and maltose. Compared with other oxidative enzymes such as glucose oxidase, hexose oxidase not only catalyse the oxidation of monosaccharides but also disaccharides are oxidised. (Biochemica et Biophysica Acta 309 (1973), 11-22).

The reaction of glucose with Hexose Oxidase is

D-glucose+H$_2$O$_2$+O$_2$→δ-gluconolactone+H$_2$O$_2$

In an aqueous environment the gluconolactone is subsequently hydrolysed to form gluconic acid.

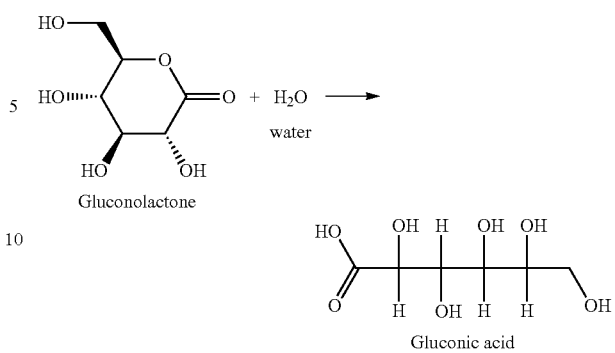

As shown, HOX oxidises the carbohydrate at the reducing end at carbon 1 and thus eliminates the possible involvement of the carbohydrate in acrylamide formation and/or acrylamide precursor formation by Amadori rearrangement or later reaction with a ketoseamine or aldoseamine to a diketoseamine or a diaminosugar respectively.

In a preferred aspect of the present invention the enzyme is capable of oxidising the sugar of the foodstuff at the 1 position. This aspect is advantageous because it ensures that the reducing sugar is oxidised such that the reducing part of the sugar is no longer available to undergo a condensation reaction with an amino acid such the Amadori reaction.

In some aspects preferably the reducing sugar is selected from lactose, galactose, glucose, xylose, mannose, cellobiose and maltose.

In some aspects the reducing sugar is lactose or galactose.

In some aspects the reducing sugar is galactose.

In some aspects preferably the foodstuff is selected from bakery goods including bread and cakes, pasta, rice, fish, sausages, meat including beef and pork, biscuits, cookies, crisp bread, cereals, pizza, beverages including coffee, and products based on potatoes, maize and flour, including potato flour and potato starch products.

In some aspects the foodstuff is a beverage.

In some aspects the foodstuff is a starch containing foodstuff.

In some aspects the foodstuff is a cereal or part of a cereal.

In some aspects preferably the foodstuff is selected from a dairy foodstuff; milk based or milk containing foodstuff, such as gratin; an egg based foodstuff; an egg containing foodstuff; bakery foodstuffs including toasts, bread, cakes; and shallow or deep fried foodstuff such as spring rolls.

When the foodstuff is a dairy foodstuff it may be cheese, such as mozzarella cheese.

In some aspects preferably the foodstuff is a potato or a part of a potato. Typical potato products in which the present invention may be applied are French fries, potato chips (crisps), coated French fries and coated potato chips, for example French fries or potato chips coated with corn starch, and potato flour and potato starch products.

The enzyme may be contacted with foodstuff during its preparation or it may be contacted with the foodstuff after the foodstuff has been prepared yet before the food stuff is subjected to conditions which may result in the undesirable acrylamide formation and/or acrylamide precursor formation. In the former aspect the enzyme will be incorporated in the foodstuff. In the later aspect the enzyme will be present on the surface of the foodstuff. When present on the surface acrylamide formation and/or acrylamide precursor formation is still prevented as it is the surface of a material exposed to drying and atmospheric oxygen which undergoes the predominant acrylamide formation and/or acrylamide precursor formation.

When contacted with foodstuff during its preparation the enzyme may be contacted at any suitable stage during its production. In the aspect that the foodstuff is a dairy product it may be contacted with the milk during acidification of the milk and precipitation of the milk curd. In this process the enzyme (such as HOX) is not active during the anaerobic conditions created during the acidification and milk protein precipitation, but will be active in the dairy product such as cheese when aerobic conditions are created. Once in aerobic conditions the enzyme oxidise the reducing sugar and reduce the tendency to acrylamide formation and/or acrylamide precursor formation.

For application of the enzyme to the surface of the foodstuff, one may apply the enzyme in any suitable manner.

Typically the enzyme is provided in a solution or dispersion and sprayed on the foodstuff. The solution/dispersion may comprise the enzyme in an amount of 1-50 units enzyme/ml, such as 1-50 units Hexose Oxidase/ml.

The enzyme may also be added in dry or powder form. When in wet or dry form the enzyme may be combined with other components for contact with the foodstuff. For example when the enzyme is in dry form it may be combined with an anticaking agent.

It will be appreciated by one skilled in the art that in the practice of the present invention one contacts the foodstuff with a sufficient amount of enzyme to prevent and/or reduce a acrylamide formation and/or acrylamide precursor formation. Typical amounts of enzyme which may be contacted with the foodstuff are from 0.05 to 50 U/g (units of enzyme per gram of foodstuff), from 0.05 to 10 U/g, from 0.05 to 5 U/g, from 0.05 to 3 U/g, from 0.05 to 2 U/g, from 0.1 to 2 U/g, from 0.1 to 1.5 U/g, and from 0.5 to 1.5 U/g.

In one preferred aspect the use/process of the present invention further comprises use of a catalase or contacting a catalase with a foodstuff to remove oxygen and thereby prevent and/or reduce acrylamide formation and/or acrylamide precursor formation (such as 2-propenal formation).

In some aspects the foodstuff contains an amino acid. In some aspects the amino acid is asparagine. It has been identified that asparagine is particularly important in the formation of acrylamide in foodstuffs.

In a preferred aspect the enzyme prevents and/or inhibits Amadori reactions and subsequent reactions with asparagine resulting in the formation of acrylamide.

In some aspects the foodstuff contains a protein. In some aspects the foodstuff contains a peptide.

Acrylamide formation and/or acrylamide precursor formation in a foodstuff may take place during the heating thereof or may take place during storage of the foodstuff. For example acrylamide formation and/or acrylamide precursor formation can happen upon storage of any kind of seeds without heating. The enzyme of the present invention, such as HOX, may still be useful however in removing a second mole of aldose or ketose sugar which may react with the already formed Amadori product to yield the diketoseamine or diaminosugar.

Moreover the system of the present invention may prevent loss of the nutritionally important Lysine in foods.

As a further addition it may be noted that reducing sugars may play an important role in the initiation of Amadori and Maillard reactions at certain moisture levels of the foodstuff (8-12%), but that lipid auto-oxidation, which is also known to initiate Amadori reactions, becomes increasingly common at low moisture levels (6%) (McDonald 1999). Lipid oxidation may actually be the primary cause for the initiation of Amadori or Maillard reactions when reducing sugars are absent. The present enzyme, such as HOX, may serve the dual purpose of removing both reducing sugars and oxygen and thereby preventing lipid oxidation as well as sugar hydrolysis at all moisture levels.

The present invention will now be described in further detail by way of example only with reference to the accompanying figures in which:

DETAILED DESCRIPTION OF THE INVENTION

Examples

Figure 1:
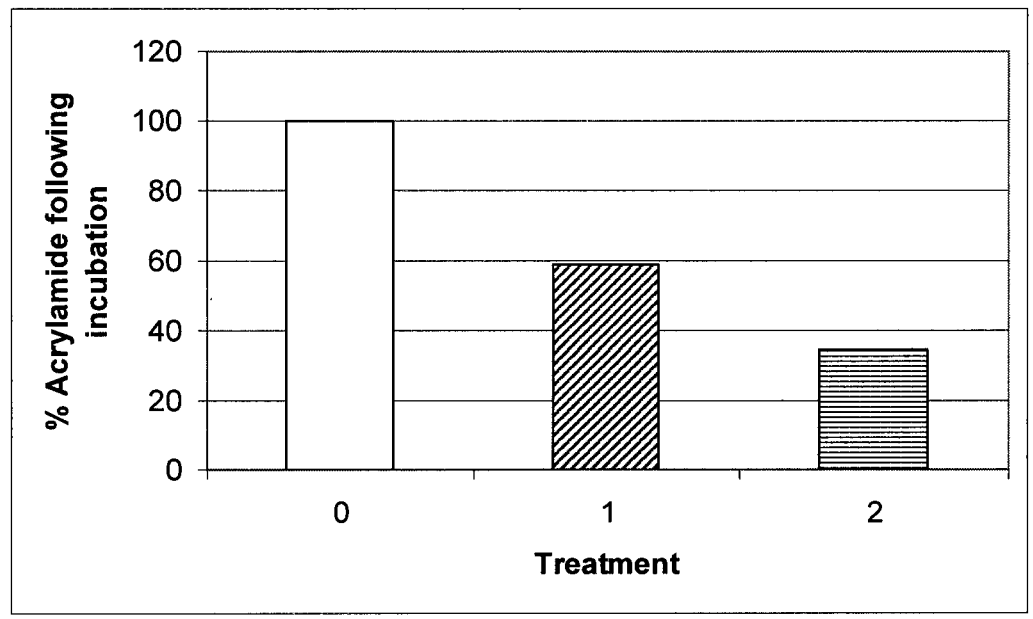
FIG. 1. Results from the use of hexose oxidase and glucose oxidase to reduce the amount of acrylamide developed by frying potato chips.

Acrylamide content of foodstuffs may be determined in accordance with J Agric Food Chem. 2002 Aug. 14; 50(17): 4998-5006.

Example 1

Pizza with Mozzarella Cheese 20 g mozzarella cheese (Karoline's Dansk mozzarella, 25% protein, 1% carbohydrate and 21% fat) is scaled in a beaker. 1 ml Hexose Oxidase solution (7.5 HOX units/ml) is sprayed onto the cheese. As a control 1 ml water is sprayed onto another sample of mozzarella cheese. The cheese is stored for 2 hours at room temperature. A dough is made from flour, salt and water. 10 g dough is scaled and placed in a petri dish. 5 grams of mozzarella cheese is placed on top of the dough and baked at 225° C. for 7 min. Another sample is baked for 15 min. After baking the samples are evaluated.

The samples in accordance with the present invention have a lower content of acrylamide than the control samples.

Example 2

The effect of hexose oxidase is tested in a gratin made by the following procedure.

75 g shortening (mp. 35° C.) and 100 g flour are heated in a pot during mixing. 350 ml skim milk (preheated to 90° C.) is added during continued mixing. Salt and pepper is added. 4 eggs are divided into yolk and egg white. The egg yolks are added individually. The egg white is whipped to a foam with 10 gram baking powder and mixed carefully into the dough. The dough is placed in 2 aluminium trays. One of the trays is sprayed with a solution of hexose oxidase 7.5 Units/ml and kept at room temperature for 30 minutes. The gratin is then baked in a air circulating oven at 175° C. for 20 minutes. After baking the gratin is evaluated.

The samples in accordance with the present invention have a lower content of acrylamide than the control samples.

Example 3

The consumption of fried potato as French fries (pommes frites) and potato chips (crisps) has increased significantly during the past two decades. One of the important parameters in the production of fried potatoes is level of reducing sugar. The level should remain low, because high level of reducing sugar contribute to higher levels of acrylamide.

In order to prevent an increase in the level of reducing sugar in potatoes during storage potatoes are often sprayed with a herbicide called chlorpropham, which prevents the potato from sprouting. Sprouting induces amylases in the potato which in turn form reducing sugars.

In this study one investigated if it is possible to reduce levels of acrylamide in fried potatoes by adding HOX to sliced potatoes before frying.

Procedure

Organic grown potatoes are used in order to ensure that no herbicides has been used. The potatoes are peeled and sliced into 2 mm thick slices using a food processor. Half of the slices are immersed in a water solution of HOX containing 100 Units/ml for 3 minutes. The other half of the potato slices are immersed in water for 3 minutes. The slices are then stored in a closed container for over night (16 hours) and then fried in vegetable oil for 2 minutes at 180° C.

Results

The samples in accordance with the present invention have a lower content of acrylamide than the control samples.

Example 4

Crisp Bread with Rye Flour 125 g rye flour
125 g flour
0.5 tsp baking powder
3 tsp sugar
2 tsp salt
100 g margarine
1.25 dl milk
1 egg Procedure Mix dry ingredients
Crumble margarine into mixture, and quickly knead the dough with water and whisked egg
Leave the dough to rest for 20 minutes, then roll it out on the plate, prick and cut it into 8×20 cm big loaves
Bake for 10 minutes at 190° C. until light brown
Break gently into pieces.

Results

The samples in accordance with the present invention have a lower content of acrylamide than the control samples.

Example 5

Determination of Glucose Oxidase and Hexose Oxidase Activity

Definition: 1 glucose oxidase (GOX) unit corresponds to the amount of enzyme which under the specified conditions results in the conversion of 1 µmole glucose per minute, with resultant generation of 1 µmole of hydrogen peroxide ($H_2O_2$).

Definition: 1 hexose oxidase (HOX) unit corresponds to the amount of enzyme which under the specified conditions results in the conversion of 1 µmole of glucose per minute, with resultant generation of 1 µmole of hydrogen peroxide ($H_2O_2$).

Assay of GOX and HOX activity in microtiter plates (300 µl).

The commonly used horse radish peroxidase dye substrate ABTS was incorporated into an assay, measuring the production of $H_2O_2$ produced by HOX or GOX respectively. ABTS serves as a chromogenic substrate for peroxidase. Peroxidase in combination with $H_2O_2$ facilitates the electron transport from the chromogenic dye, which is oxidised to an intensely green/blue compound.

An assay mixture contained 266 µl β-D-glucose (Sigma P-5504, 0.055 M in 0.1 M sodium phosphate buffer, pH 6.3), 11.6 µl 2,2'-Azino-bis(3-ethylbenzothiozoline-6-Sulfonic acid)(ABTS)(Sigma A-9941, 5 mg/ml aqueous solution), 11.6 µl peroxidase (POD)(Sigma P-6782, 0.1 mg/ml in 0.1 M sodium phosphate buffer, pH 6.3) and 10 µl enzyme (HOX or GOX) aqueous solution.

The incubation was started by the addition of glucose at 25° C. The absorbance was monitored at 405 nm in an ELISA reader. A standard curve, based on varying concentrations of $H_2O_2$, was used for calculation of enzyme activity according to the definition above.

The reaction can be described in the following manner:

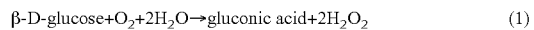

$$\beta\text{-D-glucose} + O_2 + 2H_2O \rightarrow \text{gluconic acid} + 2H_2O_2 \qquad (1)$$

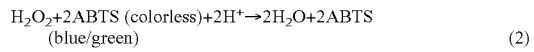

$$H_2O_2 + 2\text{ABTS (colorless)} + 2H^+ \rightarrow 2H_2O + 2\text{ABTS (blue/green)} \qquad (2)$$

Reaction (1) is catalysed by enzyme (HOX or GOX)
Reaction (2) is catalysed by enzyme (POD)

Example 6

Use of Hexose Oxidase and Glucose Oxidase to Reduce the Amount of Acrylamide Developed by Frying Potato Chips Frying Italian potatoes of the sort Nicola, were peeled and sliced into pieces of approximately (3 mm×30 mm×40 mm). Portions of approx. 30 g of sliced potatoes were treated with 40 mL of one of the incubation solutions as described below. During treatment it was made sure that all potatoes were covered with solution and the incubating beakers were stirred at RT for 4 hours in total.

After the enzyme treatment the potato slices where air dried for app. 30 min and fried for 2.5 min in pure rapeseed oil (175° C.). Subsequently the potatoes were spread on tissue paper and allowed to cool for approx. 30 min. They were stored dark in closed containers at −20° C. They were then purified and analysed as described in example 7.2.

Treatment:
- (0) 40 mL of demineralised water (=control)
- (1) 40 mL demineralised water containing 5 U/mL glucose oxidase (GOX, Sigma G-6125)
- (2) 40 mL demineralised water containing 5 U/mL hexose oxidase (HOX)

The results of the experiment are summarized in FIG. 1.

It is evident from FIG. 1 that incubation prior to frying, using an incubation solution containing either GOX or HOX, had an effect on the relative level of acrylamide found in the fried potato. The largest effect was observed using HOX (~65% reduction) (see treatment 2). A smaller effect was observed using the same dosage of GOX (~41% reduction) (see treatment 1).

Example 7

Use of Hexose Oxidase and Glucose Oxidase to Reduce the Amount of Acrylamide Developed by Baking Potato Chips 7.1. Baking Italian potatoes of the sort Nicola, were peeled and sliced as described in Example 6.

Portions of app 50 g were treated with 100 mL of incubation solution and incubated for 15 min, while stirring at RT. During treatment it was made sure that all potatoes were covered with solution.

After the enzyme treatment the potato slices where air dried for approx. 30 min and baked in a pre-heated oven for 30 min at 175° C. To account for differences in heating conditions of the oven, the baking plate was divided into 9 segments of equal size. Potatoes treated as in (1)-(3) (see below), were divided into 9 equal fractions and 1 fraction from each was placed in each segment to a total of 3 fractions per segment. This was done to minimize the chance of faulty results as a consequence of uneven heating in the oven. Subsequently the potatoes were spread on tissue paper and allowed to cool for approx. 30 min. They were stored dark in closed containers at −20° C.

Treatment:
- (1) No incubation
- (2) 100 mL demineralised water
- (3) 100 mL demineralised water containing 50 U/mL hexose oxidase (HOX)

Figure 2:
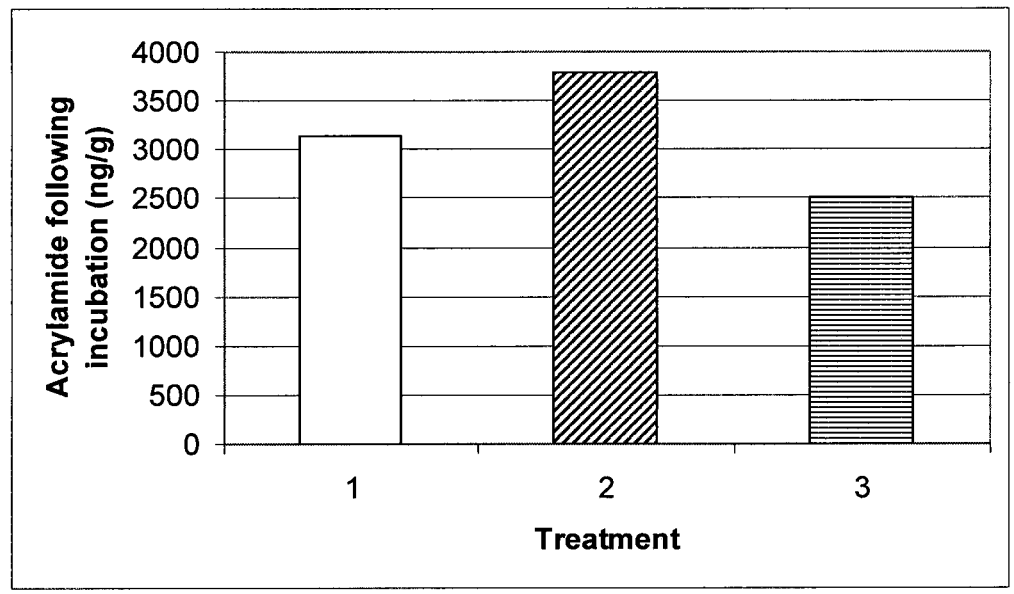
FIGS. 2 and 3. Results from the use of hexose oxidase and glucose oxidase to reduce the amount of acrylamide developed by baking potato chips.
Figure 3:
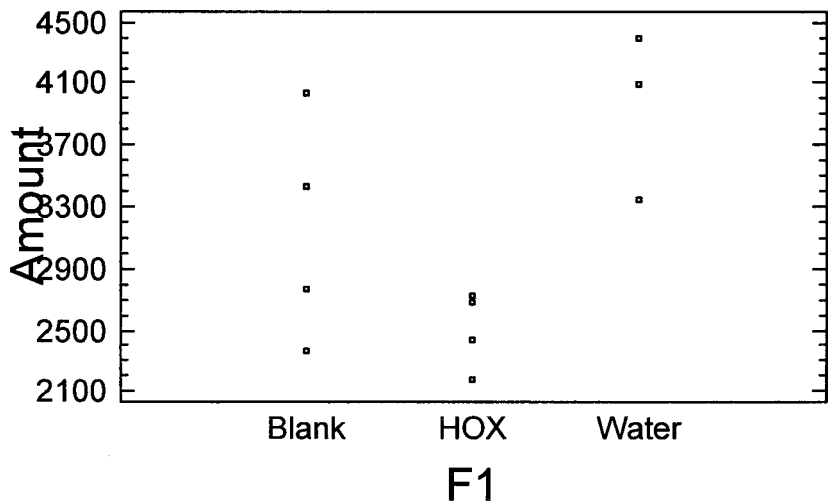

The results of the experiment are summarized in FIG. 2 and FIG. 3.

Through statistical analysis of the results in FIG. 2, it was found that HOX treated samples show significantly lower content of acrylamide compared to water treated samples.

TABLE 1

Table of Least Squares Means for Amount with 95.0 Percent Confidence Intervals

| Level | Count | Mean | Stnd. Error | Lower Limit | Upper Limit |
| --- | --- | --- | --- | --- | --- |
| GRAND MEAN | 12 | 3147.75 | | | |
| F1 | | | | | |
| Blank | 4 | 3148.0 | 272.466 | 2531.64 | 3764.36 |
| HOX | 4 | 2501.5 | 272.466 | 1885.14 | 3117.86 |
| Water | 4 | 3793.75 | 272.466 | 3177.39 | 4410.11 |

Figure 4:
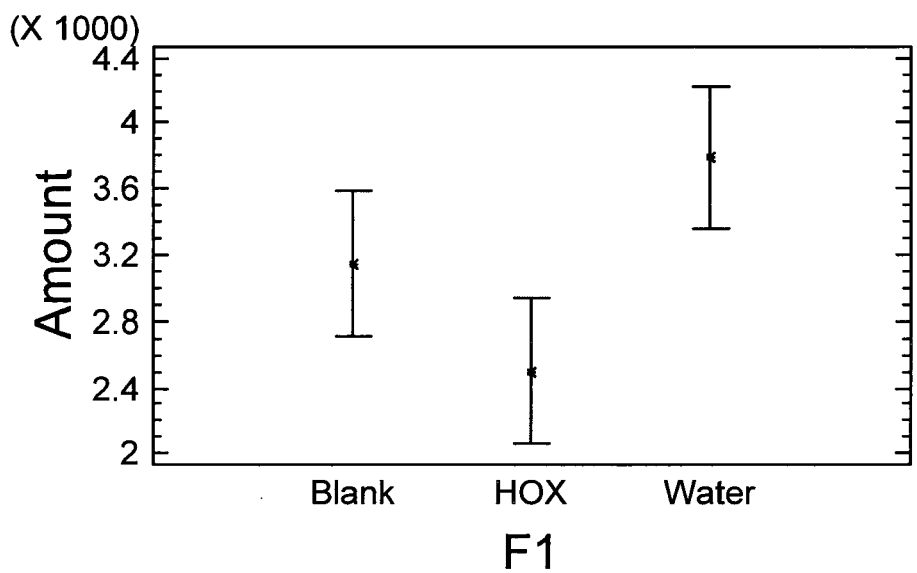
FIG. 4. Statistical analysis of the results in FIG. 2.
Figure 5:
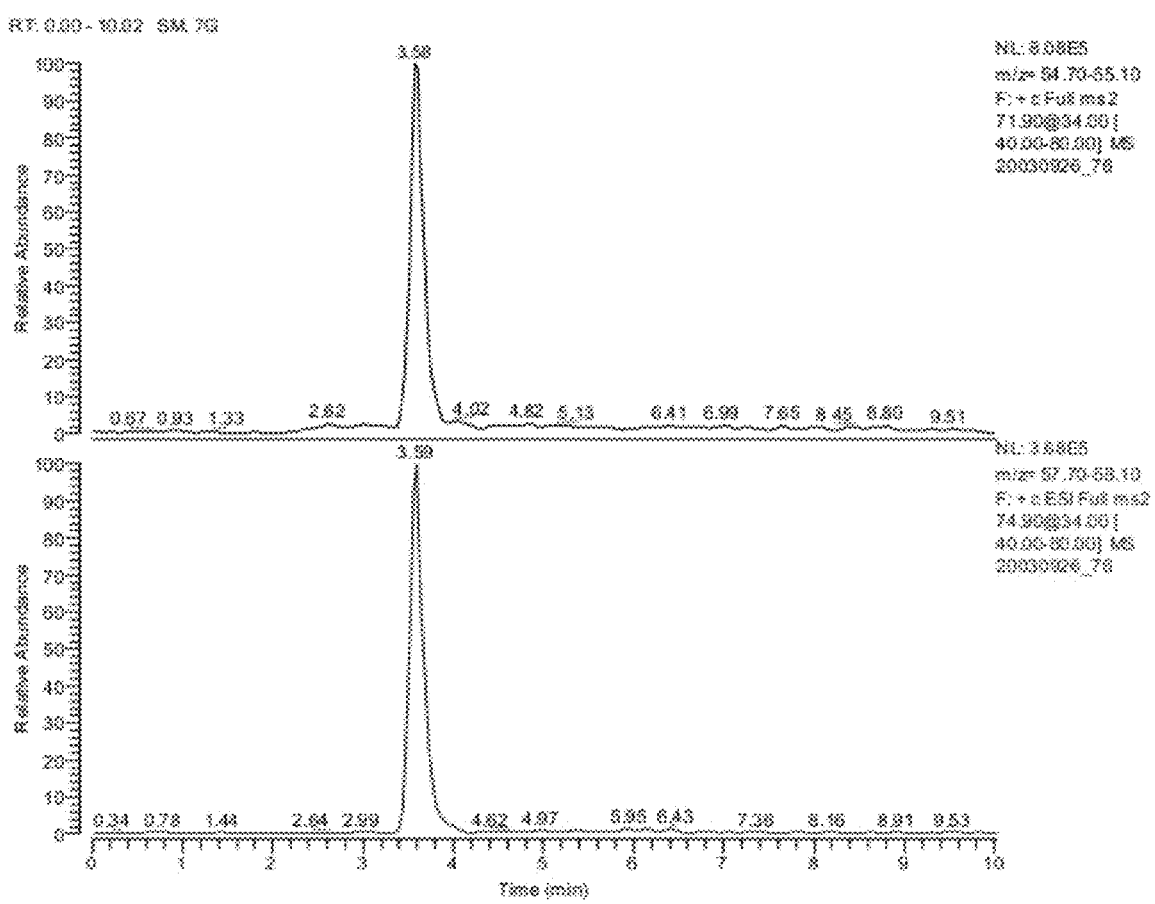
FIG. 5. SRM Chromatograms of an extract of a fried potato spiked with 1000 ng/15 ml [$^{13}C_3$]acrylamide (internal standard). The transitions monitored are m/z 72>m/z 55 (upper, acrylamide) and m/z 75>m/z 58 (lower, [$^{13}C_3$]acrylamide).

See FIG. 4

TABLE 2

Multiple Range Tests for Amount by F1

Method: 95.0 percent LSD

| F1 | Count | LS Mean | LS Sigma | Homogeneous Groups |
| --- | --- | --- | --- | --- |
| HOX | 4 | 2501.5 | 272.466 | X |
| Blank | 4 | 3148.0 | 272.466 | XX |
| Water | 4 | 3793.75 | 272.466 | X |

| Contrast | Difference | +/− Limits |
| --- | --- | --- |
| Blank − HOX | 646.5 | 871.668 |
| Blank − Water | −645.75 | 871.668 |
| HOX − Water | *−1292.25 | 871.668 |

*denotes a statistically significant difference 7.2 Sample Preparation and Quantification by LC-MS/MS Experimental Materials Methanol (Lab Scan, Dublin, Ireland), acetic acid, reagent grade ACS from Scharlau Chemie S. A. (Barcelona Spain).

Oasis MAX (6 cc, 150 mg, Part No. 186000370), Oasis MCX (6 cc, 150 mg, Part No. 186000256) from Waters (Milford, Mass., USA).

Acrylamide-1,2,3-$^{13}C_3$, 1 mg/ml methanol (Product nr. CLM-813-1.2) from Cambridge Isotope Laboratories, Inc. (MA, USA). Acrylamide (Product nr. 14857-1) from Aldrich, (Germany).

Instrumentals

The HPLC system consisted of a quaternary pump (G1311A), autosampler (G1313A), column compartment (G1316A) all from Agilent Technologies (Waldbronn, Germany).

An LCQ Deca Ion Trap mass spectrometer from Thermo Finnigan (San Jose, Calif., USA).

Column (Atlantis™ dC$_{18}$ 3 μm, 2.1 mm id.*150 mm) from Waters (Milford, Mass., USA).

Chromatographic and MS Conditions

Mobile Phase $H_2O$/MeOH/AcOH (1000/5/1 by volume)

The flow rate was 0.20 ml/min.

MS Detector Settings
- Capillary Temp (C): 275
- Sheath Gas Flow: 96
- Aux Gas Flow: 3
- Source Type: ESI
- Positive Mode
- Source Voltage (kV): 2.00
- MSn Micro Scans: 2
- MSn Max Ion Time (ms): 500

Scan Event Details:

1: Pos  (71.9) > (40.0-80.0)
   MS/MS:  Amp. 34.0%    Q 0.450  Time 30.0  IsoWidth 1.0
2: Pos  (74.9) > (40.0-80.0)
   MS/MS:  Amp. 34.0%    Q 0.450  Time 30.0  IsoWidth 1.0

Standard and Sample Preparation

Calibration standards (acrylamide) were prepared with the following concentrations: 500, 150, 50, 15, 5 ng/ml in water. The concentration of internal standard (acrylamide-1,2,3-$^{13}C_3$) was maintained at 40 ng/ml.

The sample to be analysed was coarsely ground with a knife. An aliquot (1 g) was homogenized (Ultra-Turrax T25) with 15 ml of internal standard, (ISTD, 1000 ng acrylamide 1,2,3-$^{13}C_3$/15 ml $H_2O$) in a 100 ml beaker.

The homogenate was transferred to a 50 ml centrifuge tube and 2 ml of dichloromethane were added. The mixture was shaken and centrifuged at 18000 rev/min (=25000 RCF) in a Sorvall RC-5B centrifuge for 20 min. at 4° C.

An Oasis MAX cartridge and an Oasis MCX cartridge were each conditioned with 5 ml methanol followed by 2*5 ml water. After conditioning, they were combined in series with Oasis MAX on top.

An aliquot (1.5 ml) of the supernatant (water) was passed through the Oasis MAX/Oasis MCX tandem (fraction 1).

Water (5 ml) was added to the Oasis MAX/Oasis MCX tandem and the eluent was collected in three fractions: Fraction 2 (1 ml), fraction 3 (2 ml) and fraction 4 (2 ml). Fraction 3 was filtered through a 0.45-μm filter (13 mm GHP 0.45 μm Minispike, Waters) and subjected to analysis.

Appendix 1 and Appendix 2 follow.

APPENDIX 1

Chemical Mechanisms for Acrylamide Formation

Food science and technology have had interest in acrylamide itself (and/or its derivatives incl. polymers), and its applications and possible toxic effects for many years. For example, there are many reports on can coatings and food packaging, on food additives (preservatives, artificial sweeteners etc.) and on acrylamide polymers of suitable quality with low residual acrylamide monomer levels that are used in, e.g. the U.S. for treatment of poultry, potato, corn, and other wastes, with the resulting concentrated solids used as components of blended animal feeds (14-19).

There are only a few earlier reports on the occurrence of acrylamide in foods. For example, acrylamide has been reported to be present in plant material (potatoes, carrots, radish, lettuce, Chinese cabbage, parsley, onions, spinach, and rice paddy) (20). In 1 g plant samples, 1.5.100 ng acrylamide could be detected. Acrylamide was also reported to occur in sugar (21). The origin of the detected acrylamide in these foods is not known. It might be exogenous.

To the best of our knowledge, no proposed or proven reaction routes for the formation of acrylamide during food processing have been published. Therefore, what are described below are the hypotheses we find most relevant and probable in a food processing situation.

A. Acrolein (2-propenal, CH2=CH—CHO) is a three carbon aldehyde and thus reminds the structure of acrylamide (CH2=CH—C(O)—NH2). Further, acrolein is known to be formed by:
  1. transformation of lipids
  2. degradation of amino acids and proteins
  3. degradation of carbohydrates
  4. the Maillard reaction between amino acids or proteins and carbohydrates Therefore, acrolein is a very probable precursor of acrylamide. Simple, fundamental chemical transformations (such as reaction with ammonia liberated from amino acids) can then convert acrolein (or a derivative from it) into acrylamide. The production of acrylamide through the reaction of acrolein with ammonia has been demonstrated in model systems (22).

B. Alternative formation mechanisms of acrylamide do not necessarily involve acrolein. For example, proteins and/or amino acids can after a series of transformations, such as hydrolyses, rearrangements, decarboxylations etc., eventually lead to acrylamide.

The processes mentioned above (A and B) are complicated and involve multistage reaction mechanisms which might also include free radical reactions to acrolein or acrylamide (23-25).

Acrolein Formation from Lipids

When oil is heated at temperatures above the smoke point, glycerol is degraded to acrolein, the unpleasant acrid black and irritating smoke (26-29). The formation of acrolein is known to increase with the increase in unsaturation in the oil and to lead to a lowering of the smoke point. The smoke point is higher for oils with higher content of saturated fatty acids and lower content of polyunsaturated acids. The smoke points for some of the main oils and fats are as follows: palm 240° C., peanut 220° C., olive: 210° C., lard and copra 180° C., sunflower and soybean 170° C., corn 160° C., margarine 150° C., and butter 110° C. Usually the smoke starts to appear on the surface of heated oils before their temperature reaches 175° C. The oil is first hydrolyzed into glycerol and fatty acids and then acrolein is produced by the elimination of water from glycerol by a heterolytic acid-catalyzed carbonium ion mechanism followed by oxidation (30).

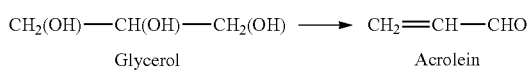

Besides the above-mentioned mechanism for the formation of acrolein from acylglycerols, acrolein can also be produced as a result of oxidation of polyunsaturated fatty acids and their degradation products (31-34). A number of aldehydic products (including malondialdehyde, C3-C10 straight chain aldehydes, and α,β-unsaturated aldehydes, such as 4-hydroxynonenal and acrolein) are known to form as secondary oxidation products of lipids (35). Acrolein was also found to form in vivo by the metal-catalyzed oxidation of polyunsaturated fatty acids including arachidonic acid (36).

Acrolein Formation from Amino Acids, Proteins and Carbohydrates

Several sources for the formation of acrolein are known. It may arise from degradation of amino acids and proteins (37, 38), from degradation of carbohydrates (39), and from the Maillard reaction between amino acids or proteins and carbohydrates (40, 41). Many possible routes for the formation of this three-carbon aldehyde—taking the starting point from many different sugars or amino acids—may be proposed. Its formation from methionine by the Strecker degradation in the frame of the Maillard reaction is one example. Alanine, with its tree-carbon skeleton, has also been suggested as a possible source. However, fission reactions of longer carbon chains are common and well-known, so at present there is no basis to give priority to any specific reaction routes.

Formation of Acrylamide Through Amino Acid Reactions not Involving Acrolein

There are also numerous, plausible reaction routes by which amino acids (or proteins) may form acrylamide without going through acrolein. Within the frame of complex, multistage reaction mechanisms, involving hydrolyses, rearrangements, decarboxylations, deaminations etc., many specific mechanistic pathways may be suggested. Decarboxylation and deamination of aspargine, and transformations of dehydroalanine (formed from e.g. serine or cysteine) are some examples of reaction routes that have been proposed.

But also in this case these can only be seen as possible examples, and similarly to above, there is no basis to give priority to any specific routes.

Conclusion

Since no systematic studies have been performed or reported, there is at present no evidence to point out any specific reaction routes for acrylamide formation, or to exclude any possibilities. Most probably a multitude of reaction mechanisms is involved, depending on food composition and processing conditions.

Further Reactions of Formed Acrolein and Acrylamide

As mentioned above, acrolein can be converted into acrylamide by a series of fundamental reactions. However, both acrolein and acrylamide are reactive, because of their double bonds and the amino group of acrylamide. They can readily react further with other reactive groups present in the food matrix or formed during the heating process. For example, acrylamide can react with small reactive molecules, such as urea ($CO(NH2)_2$) and formaldehyde (HCHO), or with glyoxal ($(CHO)2$), aldehydes (RCHO), amines ($R2NH$), thiols (RSH) etc. Furthermore, the products shown in the following scheme can even react further in the same mode of reaction.

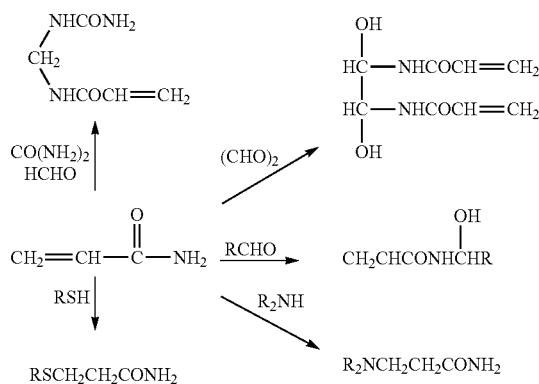

These types of reactive functional groups may also be found in macromolecules, such as proteins, for instance. (Cf adduct formation with valine in the globin chain of hemoglobin described above. In hemoglobin adducts are formed not only with valine, but also with e.g. cystein.) The presence or absence of reactive groups (or its concentration) in the food matrix may thus be one explanation of differences in final acrylamide content in different food systems. The resulting acrylamide level may be due to a balance between formation and further reactions. The low acrylamide levels in heated meat products could, for instance, depend on adduct formation between acrylamide (or acrolein) and proteins.

Factors with Possible Influence on Acrylamide Formation

A couple of different chemical mechanisms for the formation of acrylamide have been outlined above. Obviously, as long as the mechanism or mechanisms are not confirmed, the influencing factors can not be established. Thus, what is presented here are attempts to identify what factors would be of importance (regarding processing conditions or product composition) if a specific reaction route is the prevailing one. Specific emphasis is put on the Maillard reaction, since this reaction system involves many of the basic carbohydrate and amino acid reactions. Another major reaction in foods during processing, which could be of importance, is lipid hydrolysis followed by oxidation of the fatty acids.

Acrolein Formation from Lipids

Acrolein may be formed from the glycerol part of triglycerides or through oxidation of fatty acids. This means that factors favouring lipid hydrolysis as well as factors favouring lipid oxidation would promote acrolein formation. Temperature is an important factor for both these reactions. Regarding hydrolysis, pH may also be of importance and high as well as low pH may be supposed to favour acrolein formation. Regarding oxidation, lipid composition is of key importance; the higher the degree of unsaturation, the lower the stability. Protection against oxygen and light will limit the oxidation and prooxidants, such as metals, should be avoided. The protective effect of antioxidants should also be taken into account.

The Maillard Reaction as the Route for Acrylamide Formation

The Maillard reaction has been proposed as a route for acrolein formation. Also the direct formation of acrylamide through amino acid transformations has been proposed. These amino acid transformations also involve reactions common in the Maillard reaction system.

Maillard Reaction Basics

The Maillard reaction (MR) is one of the most important chemical reactions in food processing, with influence on several aspects of food quality. Flavour, colour and nutritional value may be affected and certain reaction products have been noticed to be antioxidative, antimicrobial, genotoxic etc. The practical applications of Maillard chemistry in food processing are, therefore, a matter of balance between favourable and unfavourable effects, and the aim of the food manufacturer is to find an optimum in this balance. This may be accomplished by influencing the main variables affecting the MR (42).

The Maillard reaction takes place in 3 major stages and is dependent upon factors, such as concentrations of reactants and reactant type, pH, time, temperature, and water activity. Free radicals and antioxidants are also involved (43).

The early stage (step 1) involves the condensation of a free amino group (from free amino acids and/or proteins) with a reducing sugar to form Amadori or Heyns rearrangement products. The advanced stage (step 2) means degradation of the Amadori or Heyns rearrangement products via different alternative routes involving deoxyosones, fission or Strecker degradation. A complex series of reactions including dehydration, elimination, cyclization, fission and fragmentation result in a pool of flavour intermediates and flavour compounds. Following the degradation pathway as illustrated schematically in FIG. 6, key intermediates and flavour chemicals can be identified.

Figure 6:
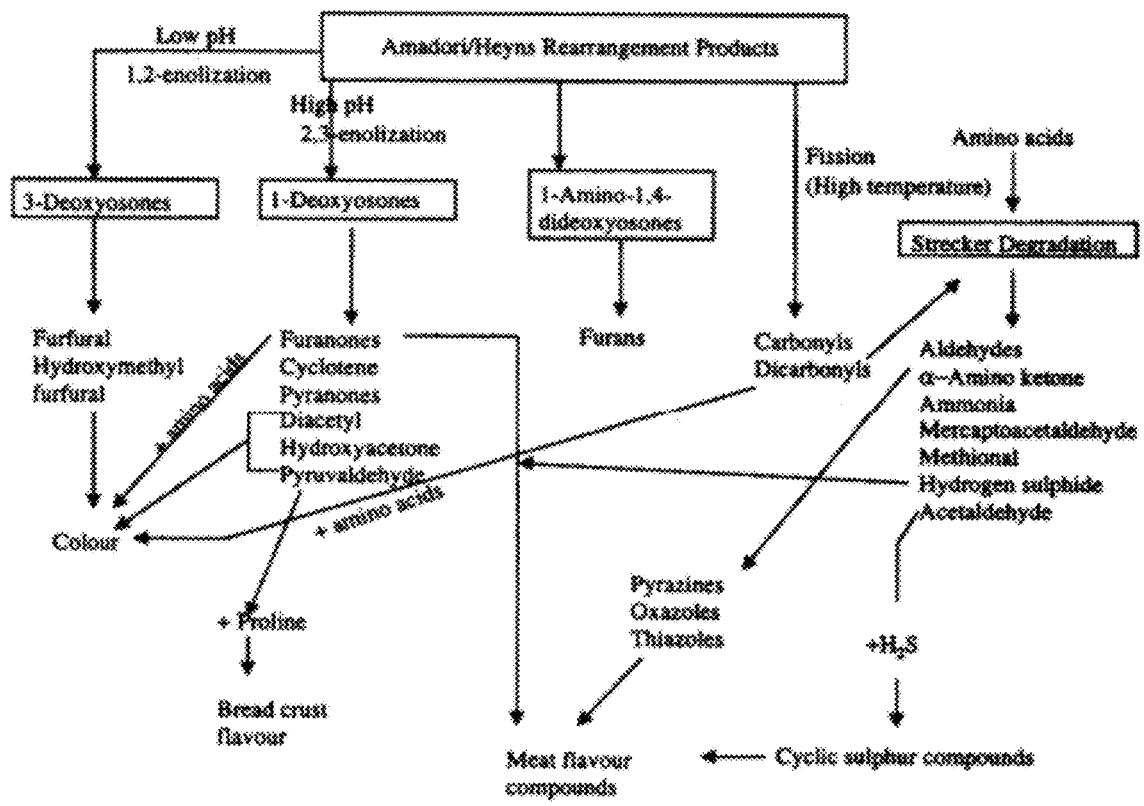
FIG. 6. Pathways of formation of key flavour intermediates and products in the Maillard reaction.

One of the most important pathways is the Strecker degradation in which amino acids react with dicarbonyls (formed by the Maillard reaction) to generate a wealth of reactive intermediates. Typical Strecker degradation products are aldehydes, e.g. formaldehyde, acetaldehyde, and possibly propenaldehyde (acrolein). Strecker degradation results in degradation of amino acids to aldehydes, ammonia and carbon dioxide (44) and takes place in foods at higher concentrations of free amino acids and under more drastic reactions, e.g. at higher temperatures or under pressure (45). Pathways of formation of key flavour intermediates and products in the Maillard reaction (43) are shown in FIG. 6.

The final stage (stage 3) of the MR is characterized by the formation of brown nitrogenous polymers and co-polymers. While the development of colour is an important feature of the reaction, relatively little is known about the chemical nature of the compounds responsible. Colour compounds can be grouped into two general classes—low molecular weight colour compounds, which comprise two to four linked rings, and the melanoidins, which have much higher molecular weights.

Review of Factors Influencing the Maillard Reaction

Factors that are particularly important for the MR are the starting reactants, e.g. type of sugar and amino acid (protein), time, temperature and water activity. Presence of metal salts (pro-oxidants), and inhibitors, like antioxidants and sulphite, might all have an impact.

Starting Reactants—Reducing Sugar and Amino Acids/Proteins

MR requires reducing sugars, i.e. sugars containing keto- or aldehydes (free carbonyl groups). The reactivity of different sugars can be summarised in the following way (46):

The shorter carbon chain, the sugar has, the greater are the lysine losses (MR).

Pentoses are more reactive than hexoses and disaccharides in yielding brown colour.

Aldoses are more reactive than ketoses both in aqueous solution model systems and at storage (low water content)

Among isomeric sugars, stereochemistry is important. Thus ribose is more reactive than xylose monitored as lysine losses.

All monosaccharides are reducing sugars. (Sugar alcohols do not participate in MR.) Among the disaccharides all sugars except sucrose are reducing sugars. In oligosaccharides and starch only the end-terminal monosaccharide is a reducing sugar. Starch and sugars, such as sucrose, lactose, maltose etc can easily hydrolyse upon heating above 100° C. at slightly acidic pH, resulting in the formation of monosaccharides (reducing sugars). Thus, thermal processing often result in a continuous supply of reducing sugar formed from complex carbohydrates.

Most studies concerning reactivity of amino acids have been performed on free amino acids in diluted aqueous solutions. The reactivity among the diamino acids increased with the length of the carbon chain. Among the amino acids studied lysine was most reactive. In proteins and peptides, only free amino groups can react, i.e. N-terminal á-amino groups and -amino groups.

Temperature and Time

The temperature dependence of chemical reactions is often expressed as the activation energy, Ea, in the Arrhenius equation. The higher the value of Ea, the more temperature dependent is the reaction rate. Activation energy data for the MR have been reported within a wide range, 10-160 kJ/mole, depending on, among other things, water activity and pH and what effect of the reaction has been measured. The temperature dependence of the MR is also influenced by the participating reactants. The temperature effect is also affected by the other variables and different aspects of the MR thus differ in temperature dependence (42).

Water

Water has both an inhibitory and an accelerating impact on the MR. Water acts partly as a reactant and partly as a solvent and transporting medium of reactants (reactant mobility). In the initial steps of the MR, 3 moles of water are formed per mol carbohydrate. Thus the reaction occurs less readily in foods with a high aw value. Water might depress the initial glucosylamine reaction, but enhance the deamination step later in the reaction.

The results from studies in model systems for optimal water concentration or water activity (free water) or relative humidity (RH) vary markedly depending on selected reactants and how the MR is evaluated—as loss in lysine or browning intensity. Several studies have been performed of which most claim the max aw to be between 0.3 and 0.7 (47). However, most data on the aw influence are based on studies at relatively low temperatures (30-60° C.). At higher temperature, more relevant to heat processes, considerably lower aw has been shown to be favourable to the MR (42).

The main explanation to an optimum reaction rate at an intermediate aw is that the reactants are diluted at the higher aw, while at a lower aw the mobility of reactants is limited, despite their presence at increased concentrations.

pH

The MR itself has a strong influence on pH. Therefore, aqueous model systems based on reflux boiling of sugars and amino acids need to be buffered since the pH quickly drops from 7 to 5. Low pH values (<7) favour the formation of furfurals (from Amadori rearrangement products), while the routes for reductones and fission products are preferred at a high pH.

However, the overall effect of pH is not clear cut, since the reactions take place by all the three pathways. In unbuffered water solutions, pH decrease during MR and buffering with alkali has a catalytic effect.

Reactivity of different amino acids at various pHs has been studied. Browning of a glucose solution upon heating was obtained first when pH exceeded 5 and it increased with increasing pH. The degree of browning varied with the position of the amino group. The function of pH is linked with specific reaction steps of the MR. Initially only non-protonised forms of amino acids a can form Schiff's base. This explains the pronounced changes in reactivity (monitored as browning) which happens when pH passes the isoelectric point of the amino group in the reacting amino acid. Thus, optimal pH for the MR varies with the system used and how the reaction is monitored (e.g. lysine losses or browning).

Inhibition of the Maillard Reaction

Measures to inhibit the Maillard reaction in cases where it is undesirable, involve lowering of the pH value, maintenance of lowest possible temperatures and avoidance of critical water contents (moistures below 30%, during processing and storage), use of non-reducing sugars, and addition of sulphite (45). The use of the inhibitor, sulphur dioxide, constitutes an important way of controlling the Maillard reaction. It may combine with early intermediates. However, sulphite only delays colour formation and it is interesting to note that the colour formed in sulphite-treated systems is less red and more yellow than in untreated systems.

Maillard Reactions and Food Processing

In exploiting the Maillard reaction, the key target for the food industry is to understand and harness the reaction pathways enabling improvement of existing products and the development of new products. While it would be easy to assume that this means the generation of flavour and colour, not all Maillard products endow positive characteristics to foods and ingredients. The positive contributions of the MR are flavour generation and colour development. The negative aspects are off-flavour development, flavour loss, discoloration, loss of nutritional value and formation of toxic Maillard reaction products (MRPs). In applying the MR, there are challenges that are common to the food industry, independent of the type of the product. These challenges can be classified as follows: maintenance of raw material quality; maintenance of controlled processes for food production; maintenance of product quality; extension of product shelf-life (42, 43).

Flavour/Aroma

The most common route for formation of flavours via the MR comprises the interaction of á-dicarbonyl compounds (intermediate products in the MR, stage 2) with amino acids through the Strecker degradation reactions. Alkyl pyrazines and Strecker aldehydes belong to commonly found flavour compounds from MR. For example, low levels of pyrazines are formed during the processing of potato flakes when the temperature is less than 130° C., but increases tenfold when the temperature is increased to 160° C., and decreases at 190° C., probably due to evaporation or binding to macromolecules. The aroma profile varies with the temperature and the time of heating. At any given temperature-time combination, a unique aroma, which is not likely to be produced at any other combination of heating conditions, is produced. Temperature also affects the development of aroma during extrusion cooking Colour The coloured products of the Maillard reaction are of two types: the high molecular weight macromolecule materials commonly referred to as the melanoidines, and the low molecular weight coloured compounds, containing two or three heterocyclic rings (48). Colour development increases with increasing temperature, with time of heating, with increasing pH and by intermediate moisture content (aw=0.3-0.7). Generally, browning occurs slowly in dry systems at low temperatures and is relatively slow in high-moisture foods. Colour generation is enhanced at pH>7. Of the two starting reactants, the concentration of reducing sugar has the greatest impact on colour development. Of all the amino acids, lysine gives the largest contribution to colour formation and cysteine has the least effect on colour formation.

Antioxidative Capacity

There are several reports on the formation of antioxidative MRPs in food processing. The addition of amino acids or glucose to cookie dough has been shown to improve oxidative stability during the storage of the cookies. Heat-treatment of milk product prior to spray drying has been reported to improve storage stability as has heat treatments of cereals (42).

The antioxidant effect of the MRP has been extensively investigated (49). It has been reported that the intermediate reductone compounds of MRP could break the radical chain by donation of a hydrogen atom: MRP was also observed to have metal-chelating properties and retard lipid peroxidation. Melanoidines have also been reported to be powerful scavengers of reactive oxygen species (50). Recently, it was suggested that the antioxidant activity of xylose-lysine MRPs may be attributed to the combined effect of reducing power, hydrogen atom donation and scavenging of reactive oxygen species (51).

Nutritive Value

Loss in protein quality is often associated with the MR, especially in cereal products and milk powder produced by heat-treatment. Usually the essential amino acid having an extra free amino group, e.g. lysine, is most vulnerable. If the essential amino acid also is the nutritionally limiting amino acid, the influence of MR on the protein quality is substantial. This is not a problem in cooking meat and fish, since these food items are very rich in protein. Loss of protein quality in terms of nutritional value is a more serious problems for heat-treatment and dehydration of especially cereals, milk and their mixtures (breakfast cereals, gruels, bread, biscuits), since carbohydrates dominates over proteins in these food items and the proteins levels are also generally low.

Toxic Effects

The possibilities that MPR could be mutagenic and/or carcinogenic were explored with Ames test, around 20-25 years ago. In general weak genotoxicity/mutagenic activities were found for known MPRs. Most attention over the past decades has been paid on the food mutagens found in the crust from cooked meat and fish. Chemically, these compounds belong to a class of heterocyclic amines, currently amounting to around 20 different species. Most of them have been classified as possible food carcinogens (group 2B) according to the International Agency for Research in Cancer (IARC) based on long-term studies on rodents. The precursors of the heterocyclic amines are free amino acids and for more than half of the 20 species, also creatine (a natural energy metabolite present in muscle cells only). Reducing sugars up to equimolar amounts compared with amino acids and/or creatine enhance the yields of heterocyclic amines markedly.

Thus MR and/or pyrolysis have been claimed to be important mechanisms for the formation of these heterocyclic amines, where Strecker aldehydes, pyrazines or pyridines and creatine have been suggested to play an important role. The yields of these food borne carcinogens are increasing with time and temperature, especially from 150° C. and above. The highest concentrations of heterocyclic amines are found in the crust of pan-fried, grilled or barbecued meat and fish. In addition, gravies prepared from dried meat-juice collected from pan-residues or oven-roasting could be rich in heterocyclic amines. Pro-oxidants, water activity in the optimal range for the MR, and high temperatures (200-400° C.) enhance their yield. The average daily exposure for heterocyclic amines is around 0.5 µg/day and person, with a range between 0-20 µg. Antioxidants, excess of carbohydrates, cooking temperatures below 200° C. and moisture contents above 30% reduce the occurrence of heterocyclic amines. Moreover, heterocyclic amines rarely occur in plant foods even during well-done cooking (52).

There is to our knowledge no report in the literature yet concerning acrylamide formation linked with the MR.

APPENDIX 2

Nonenzymic Browning

The nonenzymic browning or Maillard reaction is of great importance in food manufacturing and its results can be either desirable or undesirable. An example of the first kind is the brown crust formation on bread and one of the second kind is the brown discoloration of evaporated and sterilized milk. In products in which the browning reaction is favorable, the resulting color and flavor characteristics are generally experienced as pleasant. In other products, color and flavor become quite unpleasant.

The browning reaction can be defined as the sequence of events which begins with the reaction of the amino group of amino acids, peptides or proteins with a glycosidic hydroxyl group of sugars and terminates with the formation of brown nitrogenous polymers or melanoidins.

Figure 7:
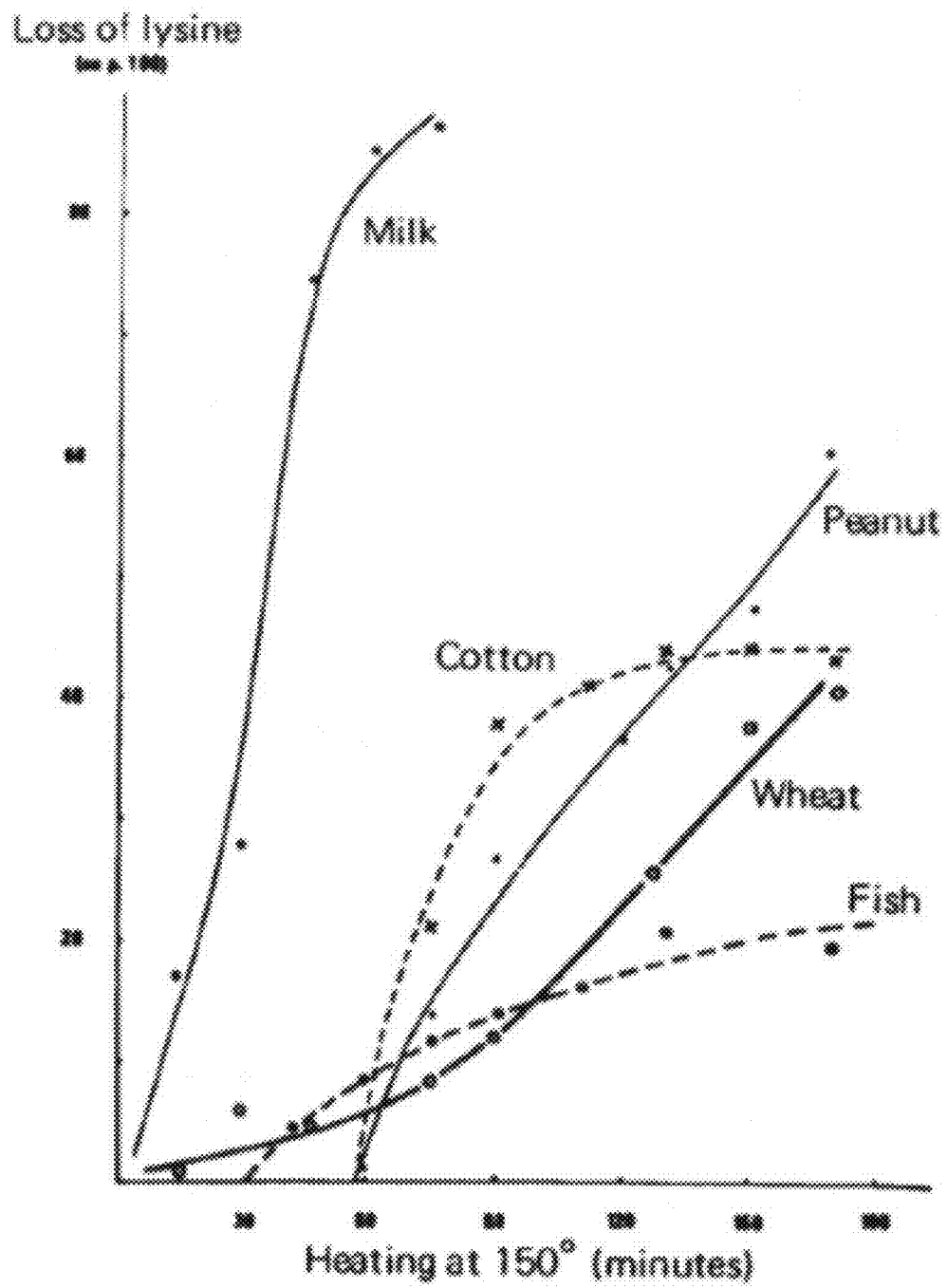
FIG. 7. Loss of lysine occurring as a result of heating of several foods.

The reaction velocity and pattern are influenced in the first place by the nature of the reacting amino acid or protein and of the carbohydrate. This means that each kind of food may show a different browning pattern. Generally, lysine is the most reactive amino acid because of the free $\epsilon$-amino group. Since lysine is the limiting essential amino acid in many food proteins, its destruction is of vital importance and can result in substantial reduction of the nutritional value of the protein. Foods which are rich in reducing sugars are very reactive, and this explains that lysine in milk is destroyed more easily than in other foods (FIG. 7). Other factors which influence the browning reaction are: temperature, pH, moisture level, oxygen, metals, phosphates, sulfur dioxide and other inhibitors.

Figure 8:
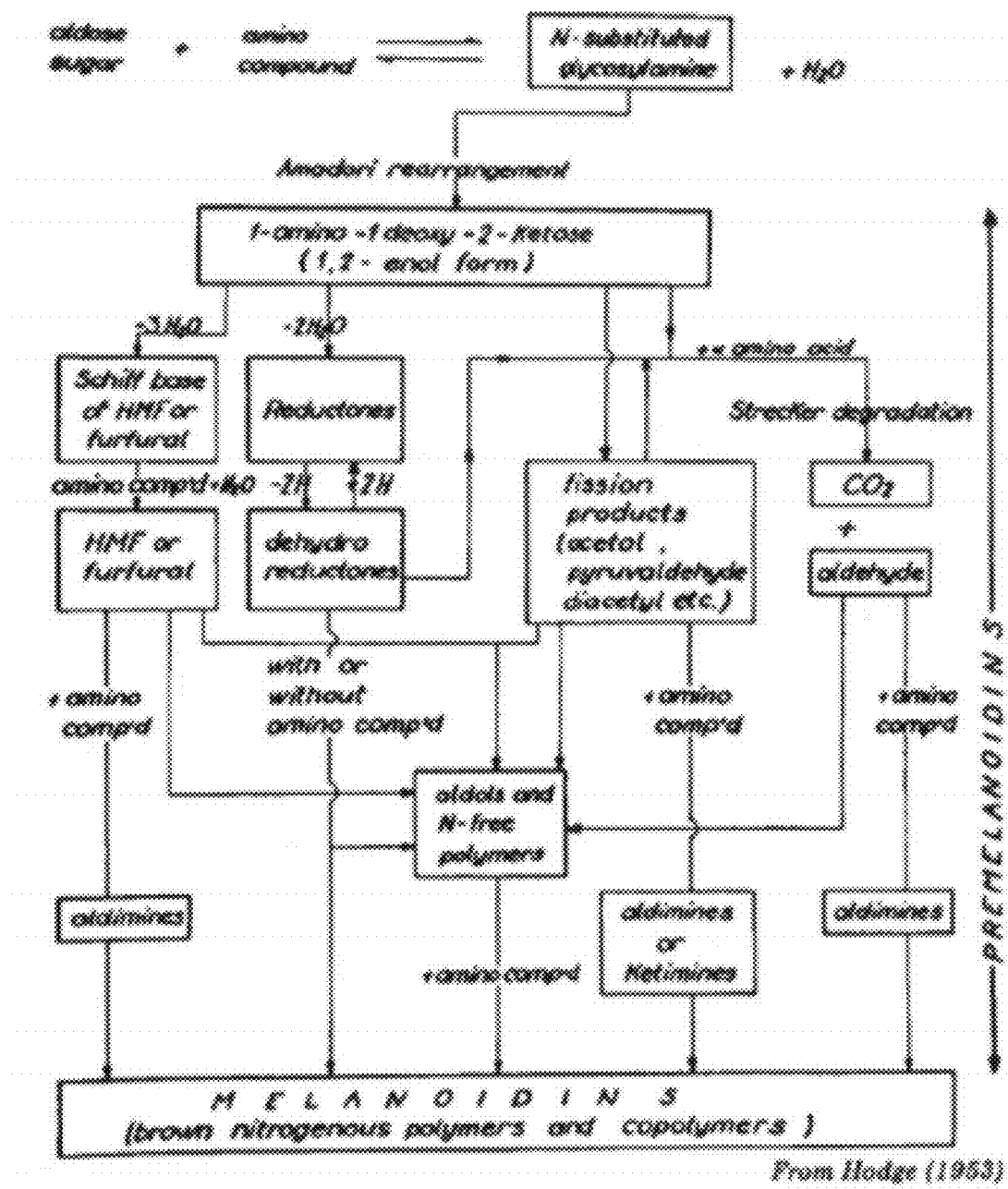
FIG. 8. Reaction pattern of the formation of melanoidins from aldose sugars and amino compounds.

The browning reaction involves a number of steps and an outline of the total pathway of melanoidin formation has been given by Hodge (1953) shown in FIG. 8. According to Hurst (1972) five steps are involved in the process:

1. The production of an N-substituted glycosylamine from an aldose or ketose reacting with a primary amino group of an amino acid, peptide or protein.
2. Rearrangement of the glycosylamine by an Amadori rearrangement type of reaction to yield an aldoseamine or ketoseamine.
3. A second rearrangement of the ketoseamine with a second mole of aldose to result in the formation of a diketoseamine, or the reaction of an aldoseamine with a second mole of amino to yield a diamino sugar.
4. Degradation of the amino sugars with loss of one or more molecules of water to give amino or nonamino compounds.
5. Condensation of the compound formed in step 4 with each other or with amino compounds with formation of brown pigments and polymers.

Figure 9:
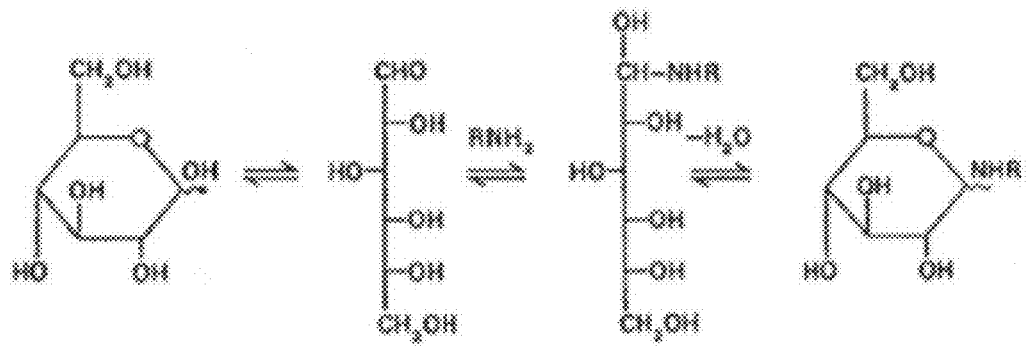
FIG. 9. Reversible formation of glycosylamines in the browning reaction.

The formation of glycosylamines from the reaction of amino groups and sugars is reversible (FIG. 9) and the equilibrium is highly dependent on the moisture level present. The mechanism as shown is thought to involve addition of the amine to the carbonyl group of the open-chain form of the sugar, elimination of a molecule of water, and closure of the ring. The rate is high at low water content and this explains the ease of browning in dried and concentrated foods.

Figure 10:
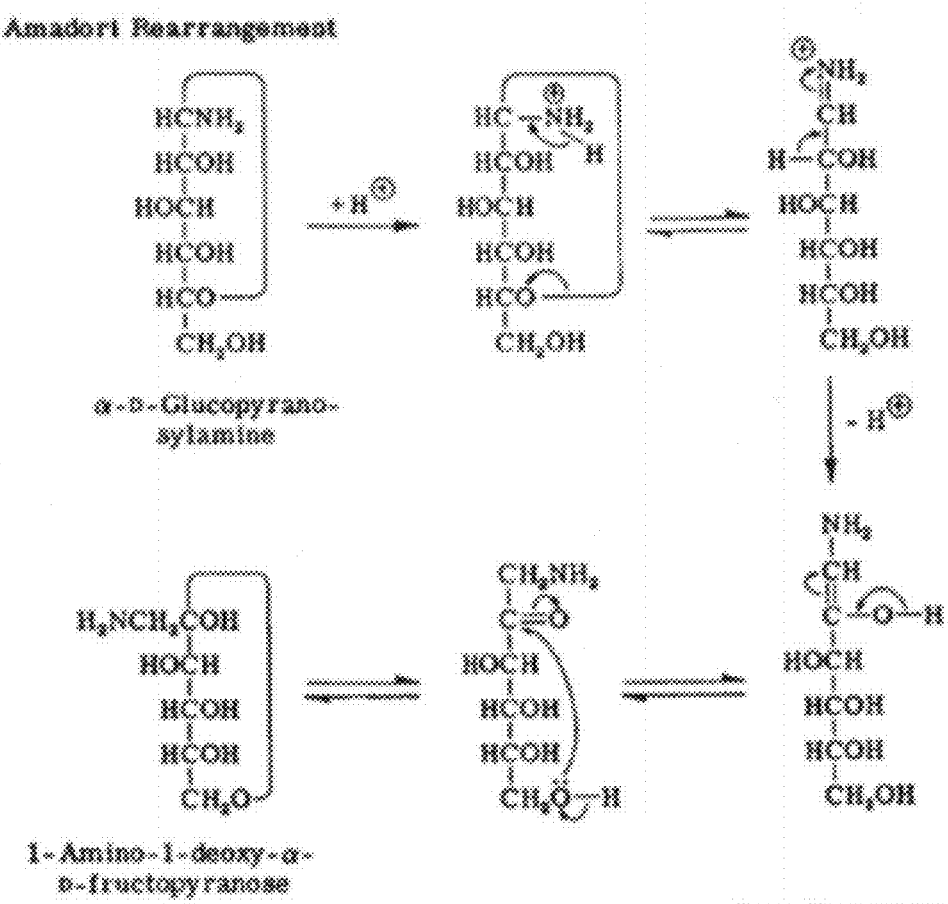
FIG. 10. Amadori rearrangement.
Figure 11:
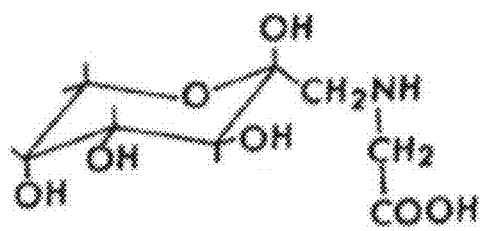
FIG. 11. Structure of 1-deoxy-1-glycin-β-D-fructose.
Figure 12:
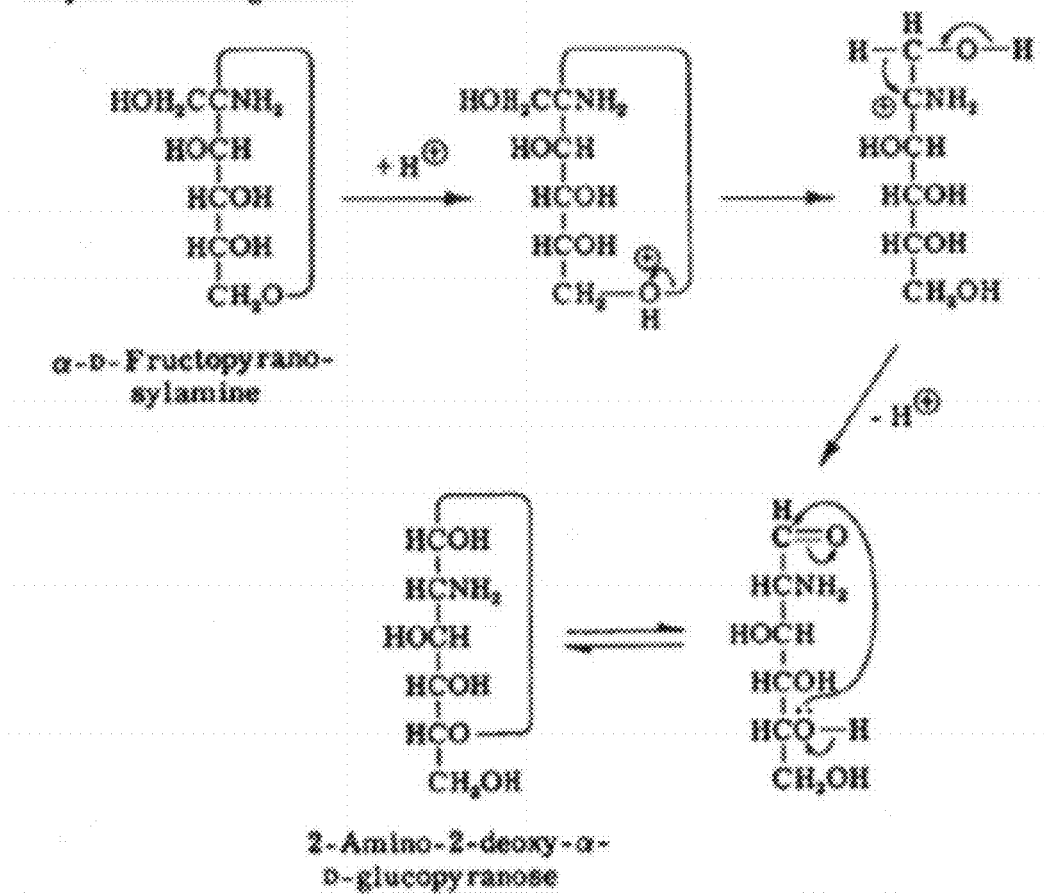
FIG. 12. Heyns rearrangement.

The Amadori rearrangement of the glycosylamines involves the presence of an acid catalyst and leads to the formation of ketoseamine or 1-amino-1-deoxyketose according to the scheme of FIG. 10. In the reaction of D-glucose with glycine the amino acid reacts as the catalyst and the compound produced is 1-deoxy-1-glycino-β-D-fructose (FIG. 11). The ketoseamines are relatively stable compounds which are formed in maximum yield in systems with 18% water content (Shallenberger and Birch 1975). A second type of rearrangement reaction is the Heyns rearrangement which is an alternative to the Amadori rearrangement and leads to the same type of transformation. The mechanism of the Amadori rearrangement (FIG. 10) involves protonation of the nitrogen atom at carbon 1. The Heyns rearrangement (FIG. 12) involves protonation of the oxygen at carbon 6.

Secondary reactions lead to the formation of diketoseamines and diamino sugars. The formation of these compounds involves complex reactions and in contrast to the formation of the primary products does not occur on a mole for mole basis.

Figure 13:
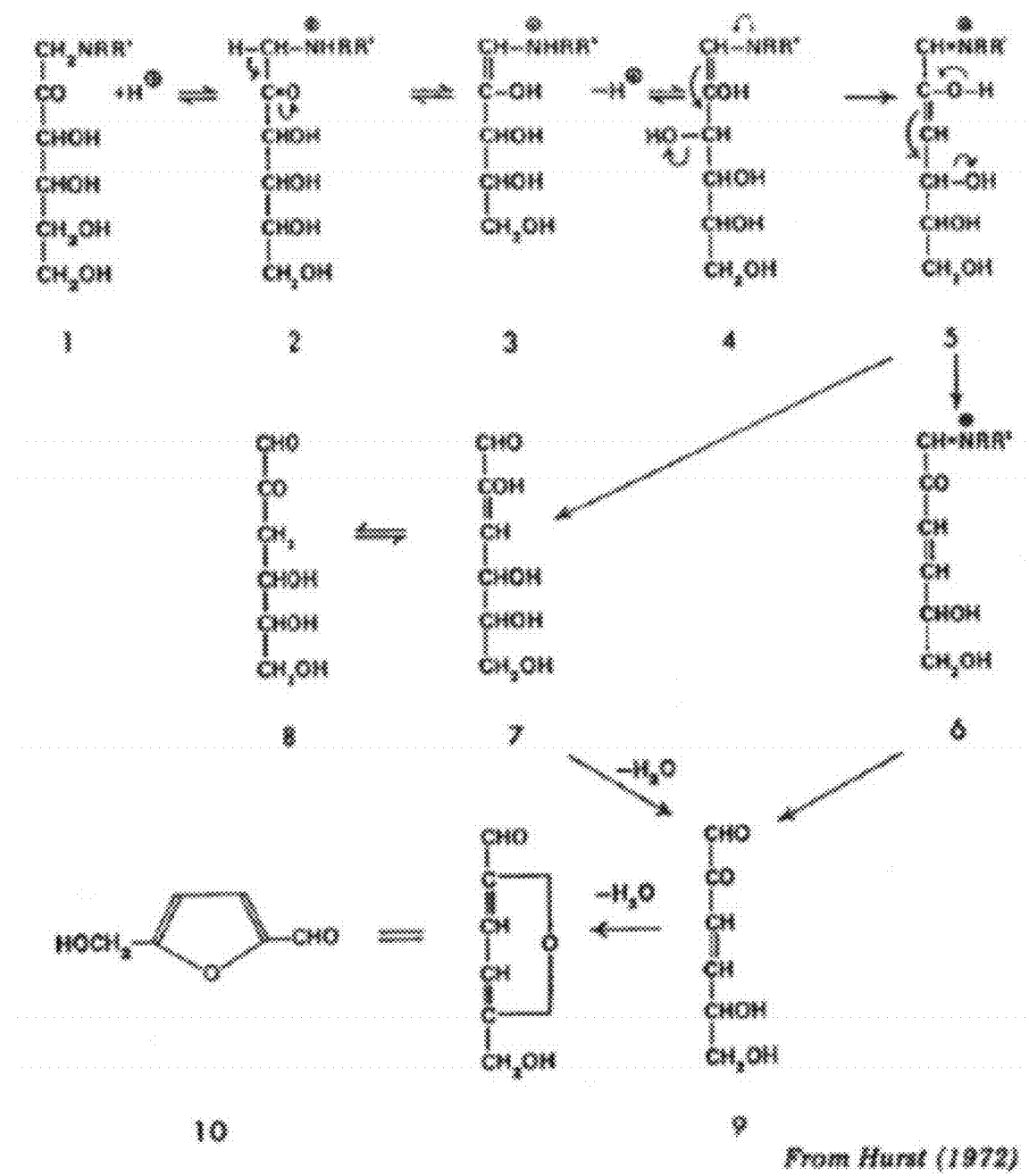
FIG. 13. 1,2-enolization mechanism of the browning reaction.

In the following step, the ketoseamines are decomposed by 1,2-enolization or 2,3-enolization. The former pathway appears to be the more important one in the formation of brown color whereas the latter results in the formation of flavor products. According to Hurst (1972), the 1,2-enolization pathway appears to be the main one leading to browning but also contributes to formation of off-flavors through hydroxymethylfurfural, which may be a factor in causing the off-flavors in stored, overheated or dehydrated food products. The mechanism of this reaction is shown in FIG. 13 (Hurst 1972). The ketoseamine (1) is protonated in acid medium to yield (2). This is changed in a reversible reaction into the 1,2-enolamine (3) and this is assisted by the N substituent on carbon No. 1. The following steps involve the β-elimination of the hydroxyl group on carbon No. 3. In (4) the enolamine is in the free base form and converts to the Schiff base (5). The Schiff base may undergo hydrolysis and form the enolform (7) of 3-deoxyosulose (8). In another step the Schiff base (5) may lose a proton and the hydroxyl from carbon No. 4 to yield a new Schiff base (6). Both this compound and the 3-deoxyosulose may be transformed into an unsaturated osulose (9), and by elimination of a proton and a hydroxyl group, hydroxymethylfurfural (10) is formed.

Following the production of 1,2-enol forms of aldose and ketose amines, a series of degradations and condensations results in the formation of melanoidins. The α-β-dicarbonyl compounds enter into aldol type condensations which lead to the formation of polymers, initially of small size, highly hydrated and in colloidal form. These initial products of condensation are fluorescent and continuation of the reaction results in the formation of the brown melanoidins. These polymers are of non-distinct composition and contain varying levels of nitrogen. The composition varies with the nature of the reaction partners, pH, temperature and other conditions.

The flavors produced by the Maillard reaction also vary widely. In some cases, the flavor is reminiscent of carmelization. An important reaction contributing to the formation of flavor compounds is the Strecker degradation of α-amino acids. The dicarbonyl compounds formed in the previously described schemes react in the following manner with α-amino acids:

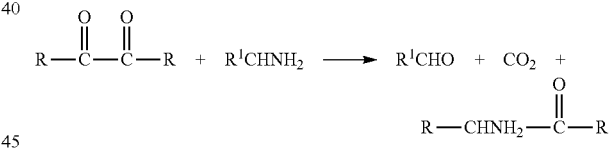

TABLE 3

AROMA AND STRUCTURE CLASSIFICATION OF BROWNED FLAVOR COMPOUNDS

| | | |
|---|---|---|
| Aromas: | Burnt | Variable |
| | (pungent, empyreumatic) | (aldehydic, ketonic) |
| Structures: | Polycarbonyls | Monocarbonyls |
| | (α,β-Unsat'd aldehydes | (R—CHO, R—C:O—CH$_3$) |
| | —C:O—C:O—, ══C—CHO) | |
| Examples of compounds: | Glyoxal | Strecker aldehydes |
| | Pyravaldehyde | Isobutyric |
| | Diacetyl | Isovsleric |
| | Mesoxalic dialdehyde | Methional |
| | Acrolein | 2-Furaldehydes |

TABLE 3-continued

AROMA AND STRUCTURE CLASSIFICATION OF BROWNED FLAVOR COMPOUNDS

| | |
|---|---|
| Crotonaldehyde | 2-Pyrrole aldehydes |
| | $C_3$-$C_6$ Methyl ketones |

Source: Hodge et al. (1972).

The amino acid is converted into an aldehyde with one less carbon atom (Schönberg and Moubacher 1952). Some of the compounds of browning flavor have been described by Hodge et al. (1972). Corny, nutty, bready and crackery-aroma compounds consist of planar unsaturated heterocyclic compounds with one or two nitrogen atoms in the ring. Other important members of this group are partially saturated N-heterocyclics with alkyl or acetyl group substituents. Compounds that contribute to pungent, burnt aromas are listed in Table 3. These are mostly vicinal polycarbonyl compounds and $\alpha,\beta$-unsaturated aldehydes. They condense rapidly to form melanoidins. The Strecker degradation aldehydes contribute to the aroma of bread, peanuts, cocoa and other roasted foods. Although acetic, phenylacetic, isobutyric and isovaleric aldehydes are prominent in the aromas of bread, malt, peanuts and cocoa, they are not really characteristic of these foods (Hodge et al. 1972).

Figure 14:
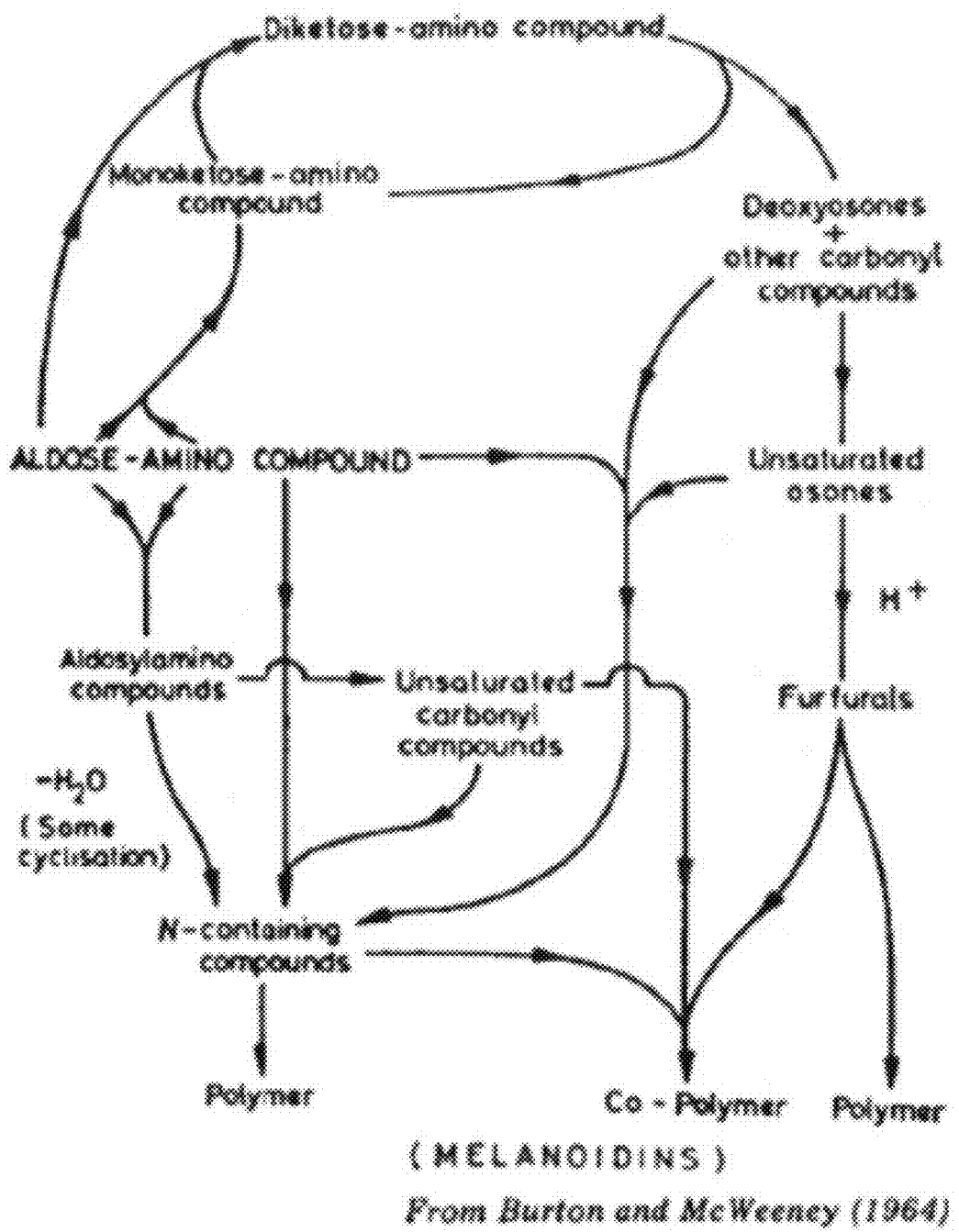
FIG. 14. Proposed browning reaction mechanism according to Burton and McWeeney.

A somewhat different mechanism for the browning reaction has been proposed by Burton and McWeeney (1964) and is shown in FIG. 14. After formation of the aldosylamine, dehydration reactions result in the production of 4- to 6-membered ring compounds. When the reaction proceeds under conditions of moderate heating, fluorescent nitrogenous compounds are formed and these react rapidly with glycine to yield melanoidins.

Figure 15:
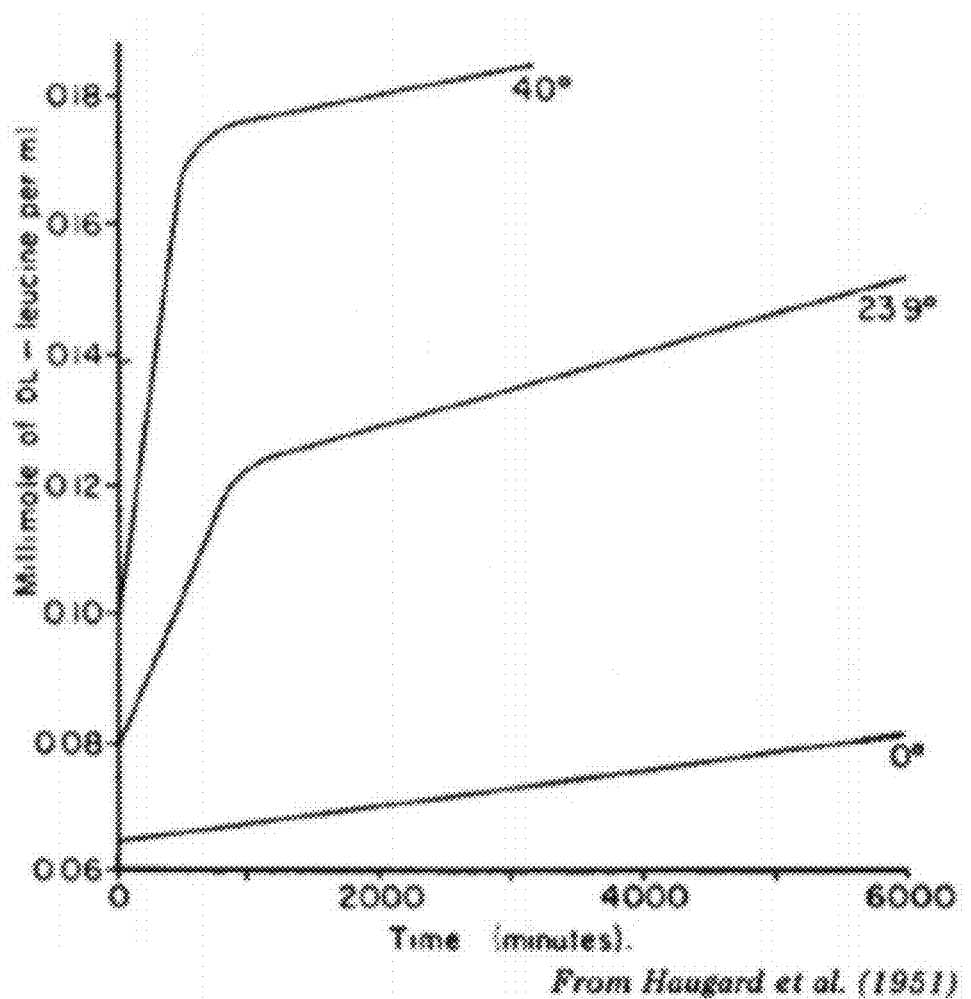
FIG. 15. Effect of temperature on the reaction rate of D-glucose with DL-leucine.

The influence of reaction components and reaction conditions results in a wide variety of reaction patterns. Many of these conditions are interdependent. Increasing temperature results in a rapidly increasing rate of browning, and not only reaction rate, but also the pattern of the reaction may change with temperature. In model systems, the rate of browning increases 2-3 times for each 10° rise in temperature. In foods containing fructose, the increase may be 5 to 10 times for each 10° rise. At high sugar contents, the rate may be even more rapid. Temperature also affects the composition of the pigment formed. At higher temperatures, the carbon content of the pigment increases and more pigment is formed per mole of carbon dioxide released. Color intensity of the pigment increases with increasing temperature. The effect of temperature on the reaction rate of D-glucose with DL-leucine is demonstrated in FIG. 15.

Figure 16:
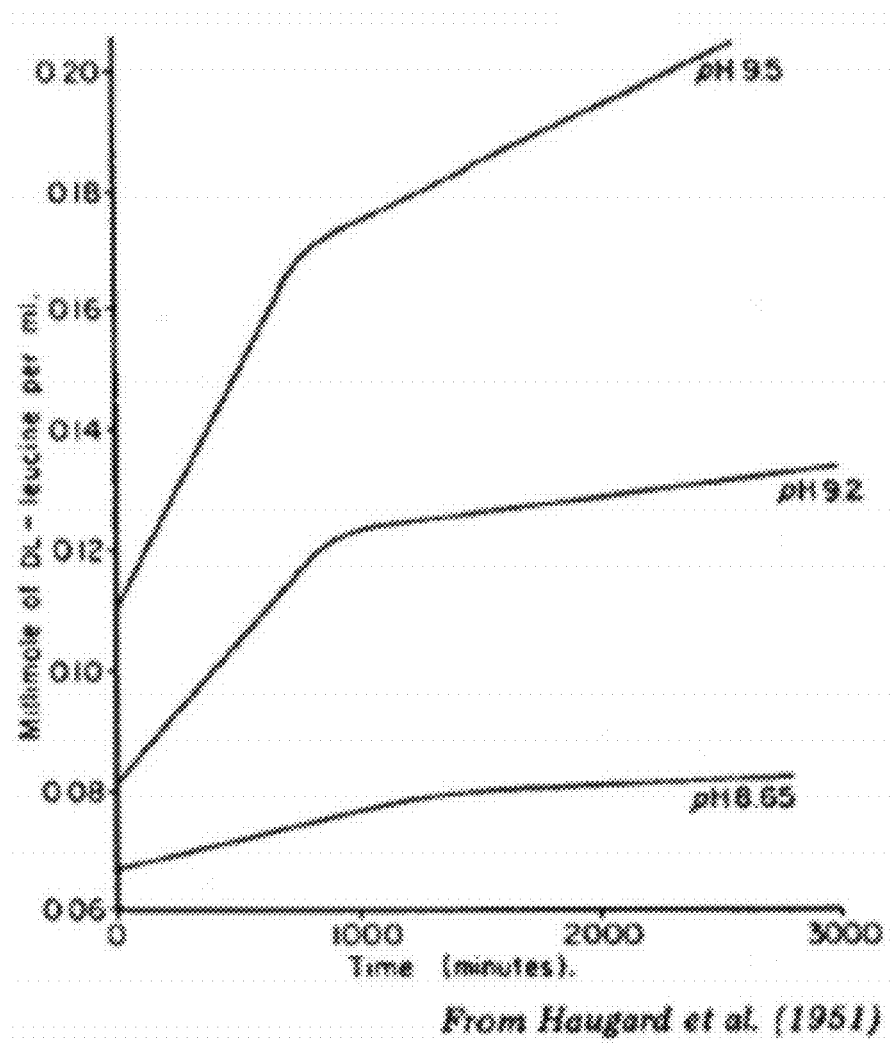
FIG. 16. Effect of pH on the reaction rate of D-glucose with DL-leucine

In the Maillard reaction, the basic amino group disappears and, therefore, the initial pH or the presence of a buffer has an important effect on the reaction. The browning reaction is slowed down by decreasing pH, and the browning reaction can be said to be self-inhibitory since the pH decreases with the loss of the basic amino group. The effect of pH on the reaction rate of D-glucose with DL-leucine is demonstrated in FIG. 16. The effect of pH on the browning reaction is highly dependent on moisture content. When a large amount of water is present, most of the browning is caused by caramelization, but at low water levels and at pH greater than 6, the Maillard reaction is predominant.

The nature of the sugars in a nonenzymic browning reaction determines their reactivity. Reactivity is related to their conformational stability or to the amount of open-chain structure present in solution. Pentoses are more reactive than hexoses, and hexoses more than reducing disaccharides. Nonreducing disaccharides only react after hydrolsys has taken place. The order of reactivity of some of the aldohexoses is mannose>galactose>glucose.

The effect of the type of amino acid can be summarized as follows. In the α-amino acid series, glycine is the most reactive. Longer and more complex substituent groups reduce the rate of browning. In the ω-amino acid series, browning rate increases with increasing chain length. Ornithine browns more rapidly than lysine. When the reactant is a protein, particular sites in the molecule may react faster than others. In proteins, the ε-amino group of lysine is particularly vulnerable to attack by aldoses and ketoses.

Methods of preventing browning could consist of measures intended to slow reaction rates, such as control of moisture, temperature or pH or removal of an active intermediate. Generally, it is easier to use an inhibitor. One of the most effective inhibitors of browning is sulfur dioxide. The action of sulfur dioxide is unique and no other suitable inhibitor has been found. It is known that sulfite can combine with the carbonyl group of an aldose to give an addition compound:

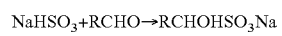

$$NaHSO_3 + RCHO \rightarrow RCHOHSO_3Na$$

but this reaction cannot possibly account for the inhibitory effect of sulfite. It is thought that sulfur dioxide reacts with the degradation products of the amino sugars which prevents these compounds from condensation into melanoidins. A serious drawback of the use of sulfur dioxide is that it reacts with thiamine and proteins, thereby reducing the nutritional value of foods. Sulfur dioxide destroys thiamine and is, therefore, not permitted for use in foods containing this vitamin.

Chemical Changes

During processing and storage, a number of chemical changes may occur in food proteins, some of which are desirable, others undesirable. Such chemical changes may lead to compounds which are non-hydrolyzable by intestinal enzymes or to modification of the peptide side chains which render certain amino acids unavailable. Mild heat treatments in the presence of water can significantly improve the nutritional value in some cases. Sulfur-containing amino acids may become more available and certain antinutritional factors such as the trypsin inhibitors of soybeans may be deactivated. Excessive heat in the absence of water can be detrimental to protein quality, e.g., in fish proteins tryptophan, arginine, methionine and lysine may be damaged. A number of chemical reactions may take place during heat treatment including decomposition, dehydration of serine and threonine, loss of sulfur from cysteine, oxidation of cysteme and methionine, cyclization of glutamic and aspartic acid and threonine (Mauron 1970).

One of the most important changes resulting in decomposition of certain amino acids is the non-enzymic browning reaction or Maillard reaction. For this reaction, the presence of a reducing sugar is required. Heat damage may also occur in the absence of sugars. Bjarnason and Carpenter (1970) demonstrated that heating of bovine plasma albumin for 27 hours at 115° C. resulted in a 50% loss of cystine and 4% of lysine. These authors suggest that amide type bonds are formed by reaction between the ε-amino group of lysine and the amide groups of asparagine or glutamine, with the reacting units present either in the same peptide chain or in neighboring ones.

Figure 17:
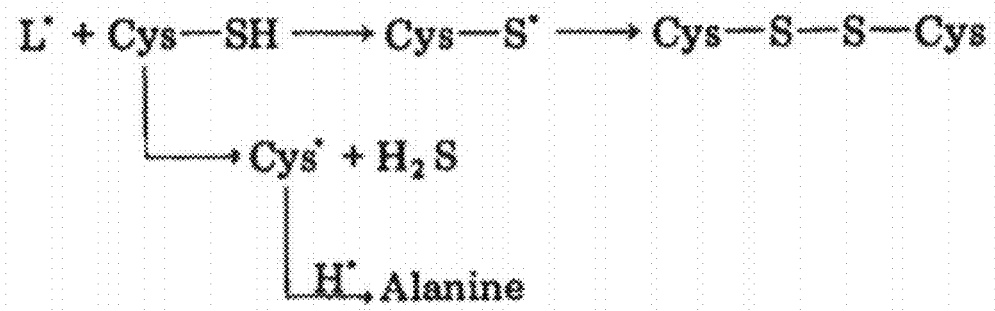
FIG. 17. Decomposition of cysteine by a lipid free radical.

Some amino acids may be oxidized by reacting with free radicals formed by lipid oxidation. Methionine can react with a lipid peroxide to yield methionine sulfoxide. Cysteine can be decomposed by a lipid free radical according to the following scheme in FIG. 17.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry or related fields are intended to be within the scope of the following claims.

The invention claimed is:

1. A process for prevention and/or reduction of acrylamide formation and/or acrylamide precursor formation in a potato or part thereof that is heated comprising contacting the potato with an enzyme prior to heating, wherein the improvement comprises the enzyme being hexose oxidase (EC1.1.3.5).

2. The process according to claim 1, wherein the potato or part thereof comprises French fries, potato chips or crisps, coated French fries, coated potato chips, potato flour or potato starch.

3. The process according to claim 2 wherein the coated French fries comprises French fries coated with corn starch or the coated potato chips comprises potato chips coated with corn starch.

4. The process according to claim 1, wherein the heating comprises frying.

5. The process according to any one of claims 1-4 wherein the hexose oxidase (EC1.1.3.5) is sprayed on the potato as a solution or dispersion.

6. The process according to claim 5 wherein the solution/dispersion comprises the enzyme in an amount of 1-50 units Hexose Oxidase/ml.

7. The process according to any one of claims 1-4 further comprising contacting the potato or potato part with a catalase.

* * * * *